(12) United States Patent
Gurfein

(10) Patent No.: US 10,556,121 B2
(45) Date of Patent: Feb. 11, 2020

(54) METHOD AND APPARATUS FOR ELECTROMAGNETIC TREATMENT OF MULTIPLE SCLEROSIS

(71) Applicant: Endonovo Therapeutics, Inc., Woodland Hills, CA (US)

(72) Inventor: Blake Taylor Gurfein, San Francisco, CA (US)

(73) Assignee: Endonovo Therapeutics, Inc., Woodland Hills, CA (US)

( * ) Notice: Subject to any disclaimer, the term of this patent is extended or adjusted under 35 U.S.C. 154(b) by 243 days.

(21) Appl. No.: 15/549,748

(22) PCT Filed: Feb. 22, 2016

(86) PCT No.: PCT/US2016/018947
§ 371 (c)(1),
(2) Date: Aug. 9, 2017

(87) PCT Pub. No.: WO2016/134367
PCT Pub. Date: Aug. 25, 2016

(65) Prior Publication Data
US 2018/0043174 A1    Feb. 15, 2018

Related U.S. Application Data

(60) Provisional application No. 62/118,933, filed on Feb. 20, 2015.

(51) Int. Cl.
*A61N 2/02*    (2006.01)
*A61N 1/40*    (2006.01)
*A61N 2/00*    (2006.01)

(52) U.S. Cl.
CPC ............. *A61N 2/02* (2013.01); *A61N 1/40* (2013.01); *A61N 2/004* (2013.01)

(58) Field of Classification Search
None
See application file for complete search history.

(56) References Cited

U.S. PATENT DOCUMENTS

2008/0097530 A1* 4/2008 Muccio ............... A61N 1/0452
607/3
2012/0116149 A1* 5/2012 Pilla ................... A61N 1/36025
600/14
2012/0302821 A1* 11/2012 Burnett ............... A61N 1/0492
600/14

* cited by examiner

*Primary Examiner* — Christine H Matthews
*Assistant Examiner* — Joshua Daryl D Lannu
(74) *Attorney, Agent, or Firm* — Dennis IP Law Group LLC; W. Dennis Drehkoff

(57) ABSTRACT

Methods and apparatuses (including systems, devices, etc.) for the treatment of neurological disorders, and particularly multiple sclerosis (MS) by the application of electromagnetic fields (EMF), and in particular, pulsed electromagnetic fields (PEMF), including a subset of PEMF in a radio frequency domain (e.g., pulse-modulated radio frequency or PRF). This treatment may prevent or delay the onset, and/or may reduce the severity of the onset of MS and MS-related symptoms.

34 Claims, 12 Drawing Sheets

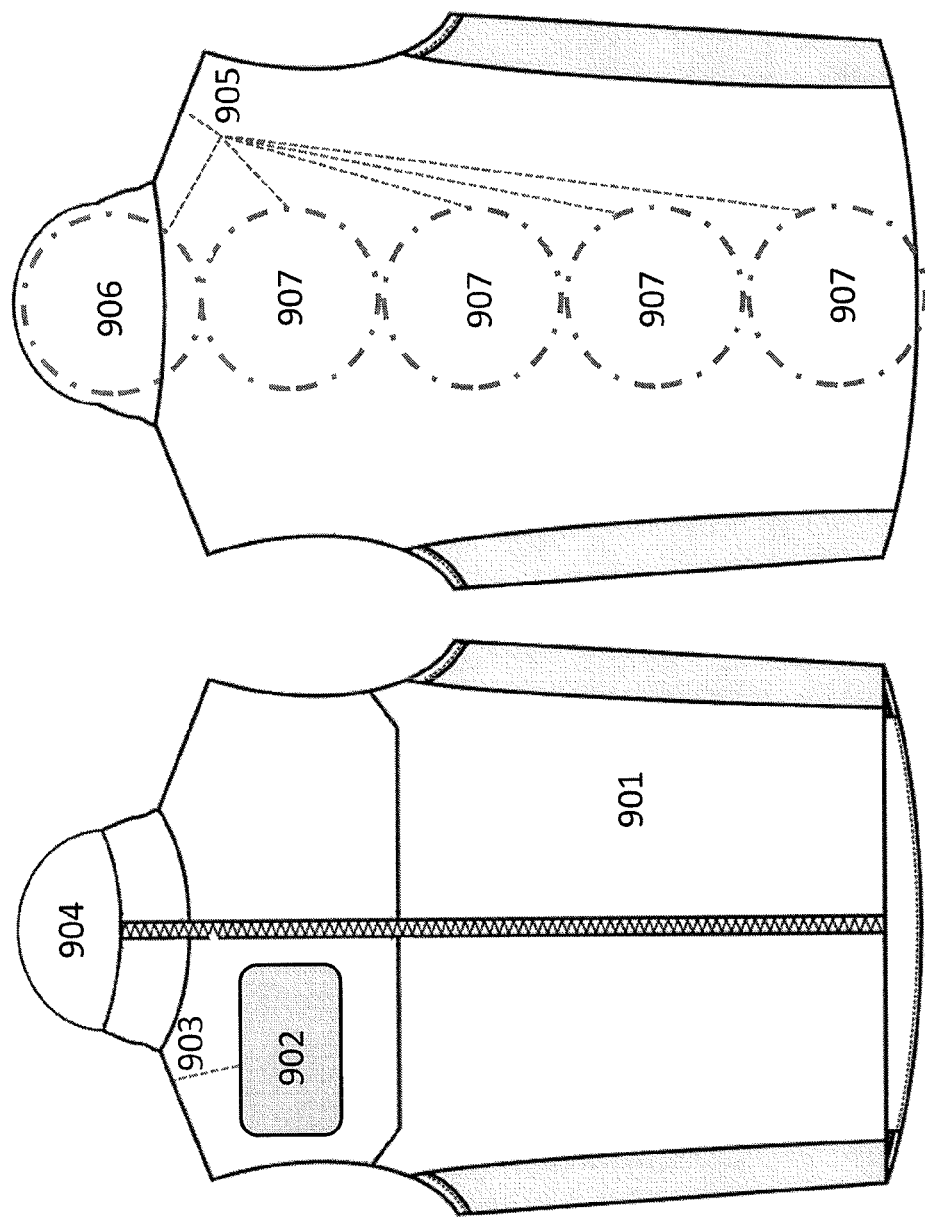

METHOD AND APPARATUS FOR ELECTROMAGNETIC TREATMENT OF MULTIPLE SCLEROSIS

CROSS REFERENCE TO RELATED APPLICATIONS

This patent application claims priority to U.S. provisional patent application No. 62/118,933, titled "METHOD AND APPARATUS FOR ELECTROMAGNETIC TREATMENT OF MULTIPLE SCLEROSIS", filed on Feb. 20, 2015.

This patent may be related to one or more of U.S. patent application Ser. No. 14/354,587, filed on Apr. 27, 2014 (published as US-2014-0303425), which claimed priority to U.S. provisional patent application 61/556,068, filed Nov. 4, 2011, and titled "METHOD AND APPARATUS FOR ELECTROMAGNETIC TREATMENT OF COGNITION AND NEUROLOGICAL INJURY"; and U.S. provisional patent application 62/106,645 filed Jan. 22, 2015, and titled "METHOD AND APPARATUS FOR ELECTROMAGNETIC TREATMENT OF MULTIPLE SCLEROSIS," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are electromagnetic treatment devices, systems and methods for the treatment of multiple sclerosis (MS). Some embodiments pertain generally to a method and apparatus for therapeutic and prophylactic treatment of MS, for delaying the onset of symptom of MS, for delaying the progression of MS, or the like. Also described herein are combination therapies, including tDCS in conjunction with whole-body or focally-directed PEMF (brain, spine, lymph etc.) to treat MS.

BACKGROUND

Over the past 40 years, it has been found that the application of weak non-thermal electromagnetic fields ("EMF") can result in physiologically meaningful in vivo and in vitro bioeffects. Time-varying electromagnetic fields, comprising PEMF or PRF, ranging from several Hertz to about 100 GHz, have been found to be clinically beneficial when used as a therapy for reducing pain levels for patients undergoing surgical procedures, promoting healing in patients with chronic wounds or bone fractures, and reducing inflammation or edema in injuries (e.g. sprains).

Although PEMF/PRF therapy has been used for a variety of treatments, one challenge has been in providing a PEMF/PRF delivery device in a design configuration that accommodates the patient's injury and concurrent treatment. For example, EMF devices are difficult to use with patients who are bed-ridden, bandaged, and engaged in ongoing treatment (or monitoring) by metal-containing devices. Some embodiments of present invention provide for configurations of EMF delivery devices that can accommodate such situations where access to the injured area is limited.

Multiple sclerosis (MS) is a frequent and disabling neurological disease characterized by multifocal destruction of central nervous system myelin. The prevalence of MS in Europe is approximately 1/2000 inhabitants. The disease typically begins between the ages of 20 and 30 and affects twice as many women as men. In 80% of cases, the disease initially evolves through attacks which result completely or with sequelae in a few weeks or months (pure remitting phase or emitting phase with sequelae). However, in 40% to 70% of cases, patients who experience an initially remitting evolvement subsequently evolve towards a progressive form (secondary progressive form). In 20% of patients, the evolvement is immediately progressive without attacks (primary progressive form).

For patients who experience an evolvement via regressive attacks, the remissions are less complete over time, resulting in functional sequelae, the ability to walk being lost on average 20 years after the beginning of the disease. Thus, the conventional form of multiple sclerosis can have three evolutive modes: Relapsing-remitting form, Primary progressive form, and Secondary progressive form. The relapsing-remitting form includes exacerbations alternating with remissions during which partial or total recovery is observed. The remissions can last months or years. The exacerbations can occur spontaneously or be triggered by certain external factors, such as an infection, post-partum or certain vaccinations. In the primary progressive form, the disease evolves progressively without remissions, with the possibility of evolutive plateau during which the disease does not progress. Contrary to the cyclic tendency, there are no clear exacerbations. In the secondary progressive form, the disorder follows on from a remitting form which begins with attacks alternating with remissions, followed by a gradual progression of the disease without identifiable attacks. Pyramidal syndrome marks the beginning of (reveals) the disease in 20% of cases, and manifests itself through walking problems with high fatigability, spasticity, exaggerated reflexes in the lower limbs. At the end of the attack, the Babinski sign often remains as a sequela.

Retrobulbar optic neuritis is also an indication of the disease in close to a third of cases: it is the most evocative symptom. It manifests itself for the patient through a rapid and profound decrease in visual acuity, ocular and orbital pain, increased with eye movements, central or cecocentral scotoma and colour blindness (dyschromatopsa of the red-green axis). At the acute stage, the back of the eye is normal, and it is only after about 15 days that atrophy of the papilla occurs, testifying to the damage to the optic nerve and sometimes persistent as a sequela. The visual evoked potentials are impaired, with slowing of the P100 wave.

Sensory problems are common. They are essentially subjective: paresthesia, pins and needles, Lhermitte's sign (electric shock sensation running down the spine when flexing the neck). A posterior cordonal syndrome with deep sensory disorders is sometimes found, and more rarely involvement of the spinothalamic tract with thermalgesic anesthesia. Facial pain (or, conversely, anesthesia) is possible in the event of the trigeminal nerve being affected in its bulbar portion.

The disease may also manifest itself through: a vestibular syndrome combining rotary vertigo, nystagmus and ataxia; a cerebellar syndrome, in which demyelinated plaques are frequent in the cerebellum and in the posterior fossa, which can produce a cerebellar syndrome with an unstable upright stance, walking as if inebriated, movements which are uncoordinated, etc.; diplopia consisting of a sensation of double vision due to paralysis of one or more oculomotor muscles (internuclear ophthalmoplegia is possible in the event of involvement of the posterior longitudinal bundles, which manifests itself in the lateral gaze through an incomplete adduction of one eye associated with nystagmus of the eye in abduction); genito-sphincteric disorders are frequent and are linked to spinal cord involvement, which manifest themselves through urinary urgency (or urinary retention), constipation and impotence. These disorders are a source of acute urine retention, and urinary infections; facial paralysis; and asthenia (fatigue), a frequent symptom of multiple sclerosis, is sometimes the one which is the most debilitating.

Multiple sclerosis is generally considered to be an autoimmune disease which occurs on a particular genetic background. From the neuropathological point of view, the disease is characterized by demyelinated plaques, well-defined hypocellular regions, within which are observed a scarcity of myelin, an astrocytic gliosis and sometimes an inflammatory infiltrate which, when it is present, attests to the active nature of the disease. With time (but sometimes early on), there are also irreversible axonal lesions, the mechanism of which is poorly understood.

Thus, it is possible to distinguish two components in the physiopathology of multiple sclerosis: (1) an inflammatory component, responsible for the evolutive attacks, and beginning with the arrival of CD4+ T lymphocytes in the central nervous system (Weiner, 2004), and (2) a degenerative component, the mechanism of which is for the moment poorly understood (Chaudhuri et al., 2004) and characterized by progression with few inflammation.

Currently, MS and its associated symptoms and pathologies are treated primarily pharmacologically. However, not all subjects respond, or are capable of responding to these therapies, or of withstanding associated side effects of such agents. Thus, there is a need for other therapies, and in particular non-invasive and/or not pharmacologic therapies.

While EMF treatments have been explored for a variety of uses, the possible benefits of EMF in treating or preventing neurological injury and degenerative conditions such as MS and related conditions are relatively unknown. This is in part due to the fact that the inflammatory response in the central nervous system (CNS) differs somewhat from that of the periphery systems for which EMF signals are currently used.

Described herein are methods and apparatuses that may address the needs and concerns described above.

SUMMARY OF THE DISCLOSURE

The present invention relates to treatment of MS and related conditions, symptoms and pathologies. In particular, described herein are method and apparatuses for delaying the onset and/or severity of MS by the application of electromagnetic fields (e.g., PEMF) as described herein.

Applicant shave surprisingly discovered that PEMF comprising bursts of higher-frequency (e.g., carrier frequency) sinusoidal waves having a 10 MHz carrier frequency wherein the bursts repeat at between 0.01 and 10 Hz and a field strength of between 1 and 200 miliGauss result in a dramatic (greater than 20% increase) in efficacy over previously described PEMF signals having parameters (e.g., carrier frequencies, burst rates, burst durations and field strengths) outside of these ranges. The ranges for these parameters described herein, and particularly for the carrier frequency, burst duration and burst rate result in a marked improvement compared to stimulation outside of these ranges.

In general, the methods for treating a neurological disorder, including (but not limited to) multiple sclerosis described herein may be synchronized with a patient's circadian rhythm. As described herein, these methods may include automatically delivering doses of pulsed electromagnetic field (PEMF) stimulation while the patient is sleeping and/or during a particular portion of the patient's sleep cycle or after the patient has been sleeping for a predetermined amount of time (e.g., 30 minutes, 1 hour, 1.5 hours, 2 hours, 2.5 hours, 3 hours, 3.5 hours, 4 hours, 4.5 hours, 5 hours, 5.5 hours, 6 hours, etc.).

In general, the method for treating a neurological disorder, including (but not limited to) multiple sclerosis described herein may include varying one or more of the parameters between doses so that the patient does not habituate or desensitize to the PEMF treatment. For example, each does may have one or more parameters (e.g., carrier frequency, amplitude, burst repetition rate, burst widths, and field strength) varied by more than a fixed percentage (e.g., more than ±5%, 10%, 15%, 20%, 25%, 30%, 35%, 40%, 45%, 50%, 55%, 60%, 70%, 80%, 90%, 100%, etc. compared to the parameter value for the immediately preceding stimulation dose). The value of the parameters may be varied within prescribed boundaries. For example, burst repetition rate may be varied between 0.01 and 10 Hz, burst widths may be varied between 1 msec and 100 msec, and field strength may be varied between 1 and 200 miliGauss. The variation may be random, chaotic, or ordered (e.g., following a pattern).

Also described herein are PEMF applicator devices adapted for delivery of PEMF signals to a patient having a neurological disorder such as multiple sclerosis. Any of these apparatuses (devices and systems) may be configured to perform any or all of the treatment methods described herein. In particular, described herein are devices (including therapeutic garments, sleeping pads, etc.) for delivery of PEMF to treat multiple sclerosis.

For example, described herein are therapeutic garment device for treating a neurological condition by pulsed electromagnetic field (PEMF) stimulation, the device comprising: a torso garment configured to be worn on a subject's torso having a back and a neck portion; a plurality of wire coil PEMF applicators extending down the middle region of the back to treat the subject's spine; a neck wire coil PEMF applicator on the neck portion to treat the patient's brain stem and cervical spine; and a PEMF signal generator integrated into the torso garment configured to deliver a treatment dose comprising a PEMF signal, wherein the PEMF signal generator is connected to the plurality of wire coil PEMF applicators and the neck wire coil PEMF applicator.

Any of these devices may include a PEMF signal generator that is configured to generate the PEMF signal comprising bursts of 10 MHz carrier waves, wherein the bursts repeat at between 0.01 and 10 Hz have a field strength of between 1 and 200 miliGauss. For example, the PEMF signal generator may be configured to generate the PEMF signal comprising bursts of 10 MHz sinusoidal carrier waves, wherein the bursts repeat at between 0.1 and 5 Hz have a field strength of between 1 and 200 miliGauss. The PEMF signal generator may be configured to generate the PEMF signal comprising bursts of 10 MHz sinusoidal carrier waves having a burst width of between 5 and 20 msec, wherein the bursts repeat at 1 Hz and have a field strength of between 1 and 200 miliGauss.

The torso garment may be configured as any appropriate garment to be worn on a subject's torso, so that it covers the spine and (in some variations) back of the subject's neck or head. For example, the garment may be configured as a shirt, jacket, sweater, undershirt, blouse, or vest.

In some variations, the garment may include a power supply that is integrated into the torso garment. The power supply may include batteries (e.g., rechargeable batteries).

The neck portion may comprise a reinforced high collar. A high collar may stand between 1 and 8 inches (e.g., between 1.5 and 6 inches, between 1.5 and 5 inches, between 1.5 and 4 inches, etc.) above the neckline of the garment, e.g., relative to the shoulder portion of the garment.

In general, the device my include wiring within a fabric of the torso garment connecting the PEMF signal generator to the plurality of wire coil PEMF applicators and the neck wire coil PEMF applicator.

The applicators (e.g., wire coils) may generally be loops of flexible wire that can be shaped to conform the body. The applicators (e.g., the plurality of wire coil PEMF applicators) may form loops that are arranged adjacent to each other in a line down the back. The applicators may be attached to the outside surface, inside surface or within the garment itself. The applicator may be permanently affixed or temporarily attached to the garment.

In general, the signal generator may be adapted to provide the PEMF therapies/doses described herein. For example, the signal generator may be configured to limit the number of doses deliverable within a 24 hour period to 12 or less. The signal generator may be configured to deliver treatment doses while the patient is asleep and/or at night. For example, the devices may include a clock, and the device may automatically deliver one or more doses at night. Alternatively or additionally, the device may include one or more sensors (motion sensors, EEG sensors, other sleep stage sensors) to determine if a subject is asleep and/or what stage of sleep the subject is in, and thereby deliver one or more doses while the patient is asleep or after the patient has been asleep for a sufficiently long period of time.

For example, described herein is a therapeutic garment device for treating multiple sclerosis by pulsed electromagnetic field (PEMF) stimulation, the device comprising: a torso garment configured to be worn on a subject's torso having a back and a neck portion; a plurality of wire coil PEMF applicators extending down the middle region of the back to treat the subject's spine; a neck wire coil PEMF applicator on the neck portion to treat the patient's brain stem and cervical spine; and a PEMF signal generator integrated into the torso garment configured to deliver a treatment dose comprising a PEMF signal comprising bursts of a 10 MHz carrier wave, wherein the bursts repeat at between 0.01 and 10 Hz, and wherein the PEMF signal generator is connected to the plurality of wire coil PEMF applicators and the neck wire coil PEMF applicator.

Any of the therapeutic garments described herein may alternatively be configured as a mat or mattress upon which a patient may sleep or rest and receive dosing as described herein. The mat may include a plurality of applicators for delivering the dose(s) described herein to a patient's head, neck and/or spine while the patient is laying on the mat.

As mentioned above, also described herein are methods of treating a patient having multiple sclerosis, the method comprising delivering a dose of pulsed electromagnetic field (PEMF) stimulation comprising bursts of a 10 MHz carrier wave, wherein the bursts repeat at between 0.01 and 10 Hz, from one or more PEMF coils positioned against one or more of the patient's head, neck and spine, wherein the field strength of between 1 and 200 miliGauss.

Delivering the PEMF stimulation may include delivering the PEMF stimulation comprising bursts repeating at 1 Hz, and/or bursts having a 10 msec burst width. The dose may be limited to 15 minutes or less (and/or between one and 12 times a day).

As mentioned, delivering the PEMF stimulation may include automatically delivering the dose while the patient is sleeping. For example, any of these methods may include determining the patient's sleep state and delivering the PEMF stimulation while the patient is sleeping.

Any of the methods described herein may also include applying a plurality of additional doses without desensitizing the patient, wherein the additional doses each have different parameters for one or more of: burst repetition rate, burst widths, and field strength. The additional doses may each have different parameters for one or more of: burst repetition rate between 0.01 and 10 Hz, burst widths between 1 msec and 100 msec, and field strength between 1 and 200 miliGauss.

Stimulation may include delivering the dose of PEMF stimulation from a plurality of PEMF coils positioned against one or more of the patient's head, neck and spine. Stimulation may include delivering the dose of PEMF stimulation from a plurality of loops of PEMF coils that are arranged adjacent to each other in a line down the patient's back.

A method of treating a patient having multiple sclerosis may include automatically delivering a dose of pulsed electromagnetic field (PEMF) stimulation while a patient is sleeping, wherein the PEMF stimulation comprises bursts of a 10 MHz carrier wave repeated at between 0.01 and 10 Hz, and the field strength is between 1 and 200 miliGauss, further wherein the PEMF stimulation is delivered from a plurality of PEMF coils positioned against one or more of the patient's head, neck or spine.

BRIEF DESCRIPTION OF THE DRAWINGS

FIGS. 9A and 9B show another example of an apparatus, configured as a wearable garment, for treating a patient with MS as described herein. FIG. 9A is a front view and FIG. 9B is a back view.

DETAILED DESCRIPTION

Figure 1A:
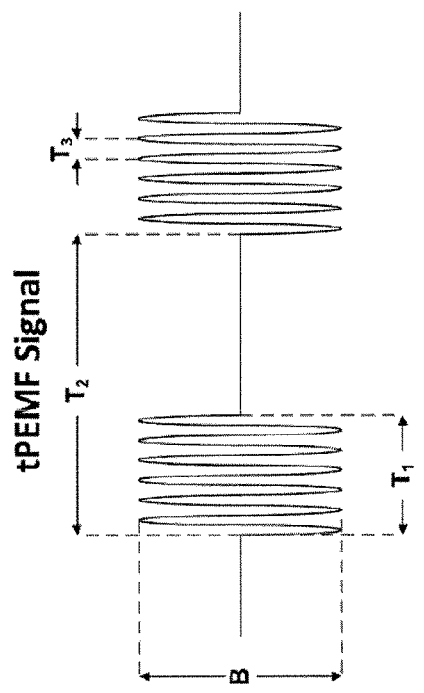
FIG. 1A is an example of a PEMF waveform.

In general, described herein are methods and apparatuses (including systems, devices, etc.) for the treatment of neurological disorders, and particularly multiple sclerosis (MS) by the application of electromagnetic fields (EMF), and in particular, pulsed electromagnetic fields (PEMF), including a subset of PEMF in a radio frequency domain (e.g., pulse-modulated radio frequency or PRF). The data provided herein suggests that this treatment may prevent or delay the onset, and/or may reduce the severity of the onset of MS and MS-related symptoms.

In addition, the methods and devices described herein may deliver combination therapies, including tDCS in conjunction with whole-body or focally-directed PEMF (brain, spine, spleen, lymph nodes, etc.).

In some variations the PEMF signal applied may be directed to the management of the MS disease process, and electrical NIBS may be directed to address acute fatigue. In some variations, PEMF (e.g., tPEMF) may reduce, forestall or eliminate the acute phases of MS, which may result in a concomitant reduction/elimination in associated symptoms, such as fatigue.

Some embodiments described herein are devices, systems and methods for delivering electromagnetic signals and fields to individuals at risk of MS. Some embodiments described provide for headgear such as flexible, lightweight coils that form part of an electromagnetic field treatment device. The headgear may include a sensor configured to measure a parameter of the environment or the user. The sensor can also be configured to automatically trigger activation of the treatment device and delivery of the electromagnetic field to the user. The sensor may be prompt activation of the treatment device once the sensor measures a sensed value that satisfies or exceeds a predetermined threshold value.

Some embodiments provide for an apparatus for delivering electromagnetic treatment comprising an applicator having a single coil (e.g., flexible coil wire of diameter between 4 inches and 18 inches, etc.). Some variations incorporate a plurality coils positioned to apply EMF to a single body region or to a combination of body regions to treat MS. These apparatuses (e.g., devices) may be configured as a garment to be worn on a subject's torso, and/or neck and/or head. In some variations the applicators are integrated into a mattress, bed, or other furniture onto which the subject may sit, recline, etc.

Optionally, in any of the preceding embodiments, the electromagnetic treatment device includes an applicator configured to deliver a therapeutic electromagnetic field to the user's body (e.g., head, spine, both) and a control circuit controlling a generator configured to provide an electromagnetic signal to the applicator to induce the therapeutic electromagnetic field with a sequence and regimen appropriate to the therapeutic need.

Optionally, in any of the preceding embodiments, the electromagnetic signal can comprise a carrier signal having a frequency in a range of about 0.01 Hz to about 10,000 MHz and a burst duration from about 0.01 to about 1000 msec. More preferably, the carrier signal is between 8 MHz and 12 MHz, or most preferably at or around 10 Mhz.

Optionally, in any of the preceding embodiments, the sensor is an accelerometer and/or a pressure sensor, which may confirm patient contact and/or sleep state. In general, any of these apparatuses may include one or more sensors for determining sleep state.

Optionally, in any of the preceding embodiments, the electromagnetic treatment device may be configured to apply a pre-programmed treatment protocol.

Optionally, in any of the preceding embodiments, the apparatus (e.g., garment and/or headgear, mattress, pad, etc.) includes an alert means for indicating that the electromagnetic treatment device is active.

Optionally, in any of the preceding embodiments, the electromagnetic treatment device is removable from the apparatus (wearable, such as torso-worn garment, headwear, hat, helmet, etc., or furniture, e.g., mattress, pad, etc.). In other embodiments, the electromagnetic treatment device is incorporated into the wearable and/or furniture.

Optionally, in any of the preceding embodiments, the electromagnetic treatment device is configured to generate the electromagnetic signal through an electrode separated from a target tissue location by an air gap.

Optionally, in any of the preceding embodiments, the applicator is configured to contact the user's skin.

Optionally, in any of the preceding embodiments, the electromagnetic treatment device comprises a replaceable or rechargeable power source.

Optionally, in any of the preceding embodiments, a remote control element is included and configured to operate the electromagnetic treatment device.

Optionally, in any of the preceding embodiments, the applicator comprises pliable and conformable coils having a generally circular shape.

Optionally, in any of the preceding embodiments, the applicator has a diameter between about 2 inches to about 8 inches.

Optionally, in any of the preceding embodiments, the applicator is adjustable.

Optionally, in any of the preceding embodiments, the applicator comprises a flexible band configured to electrically and physically couple to the circuit control generator.

Optionally, in any of the preceding embodiments, the applicator comprises a collapsible wire having a retracted and extended position.

Optionally, in any of the preceding embodiments, the applicator is removably attached to the headwear or helmet with a fastening mechanism.

Optionally, in any of the preceding embodiments, the applicator comprises conductive ink.

Optionally, in any of the preceding embodiments, a connecting member is included between the applicator and the control circuit. Optionally, in any of the preceding embodiments, a connecting member comprises a pliable material adapted to allow the applicator and the control circuit to move relative to each other.

Optionally, in any of the preceding embodiments, a processor is included and configured to collect and record user information while the apparatus is worn.

Optionally, in any of the preceding embodiments, the electromagnetic device is configured to emit a pulse-modulated radio frequency signal with a carrier frequency of approximately at 10 MHz at a 10 msec burst repeating at about 0.1-5 bursts/sec (e.g., 0.1-5 Hz, and preferably 1 Hz). Optionally, in any of the preceding embodiments, the electromagnetic signal comprises a carrier signal at about 10 MHz.

For example, FIG. 1A illustrates one example of a PEMF signal that is delivered by a PEMF apparatus to a patient. In this example, the PEMF signal (or tPEMF signal) includes a plurality of bursts of duration $T_1$, having a repetition rate of $1/T_2$, of a carrier frequency (1/T3) and a peak induced magnetic field of (B) and peak induced electrical field (E). For example, described herein are optimal PEMF signals having a carrier frequency of approximately 10 MHz and burst durations of 10 msec ($T_1$=10 msec) at 1 burst/sec (1 Hz rep rate, $1/T_2$). The peak induced magnetic field (B) is typically between 1 and 200 miliGauss.

Figure 1B:
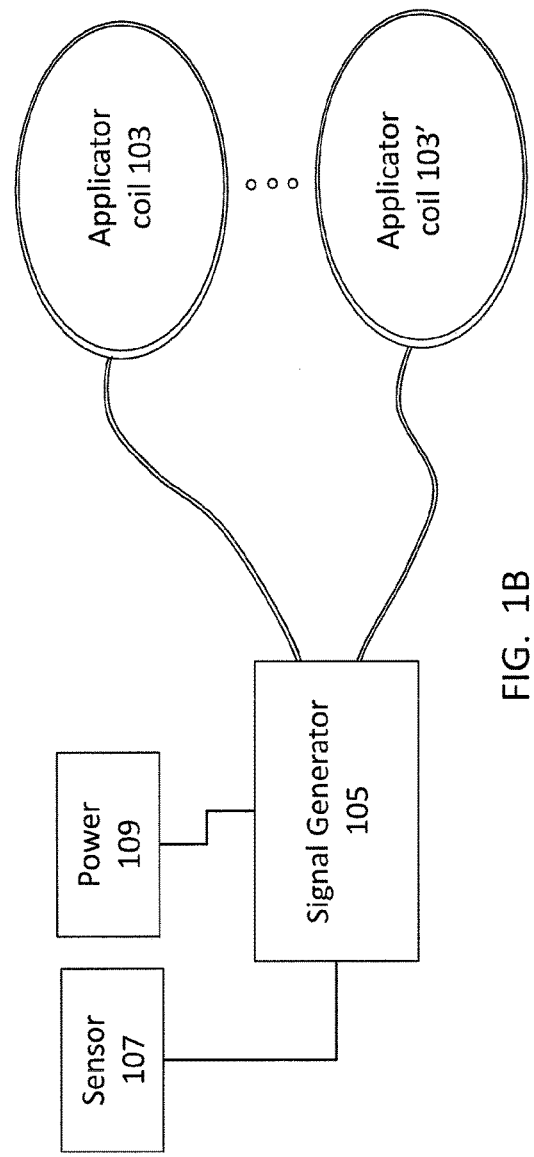
FIG. 1B is a schematic illustration of an apparatus for delivering PEMF waveforms as described herein.

FIG. 1B illustrates a schematic of a PEMF device that may be used as described herein to treat multiple sclerosis. For example, the apparatus may include one or more (e.g., a plurality of 2, 3, 4, 5, 6, 7, 8, 9, etc.) of applicators comprising a wire coil 103, 103', a signal generator 105 to which the applicators are connected (e.g., by wires). The signal generator typically generates a signal for delivery by the one or more applicators and may be connected to a power source 109. One or more sensors (e.g., sleep state sensors (e.g., accelerometers, EEG sensors, galvanic skin sensors, etc.) 107 may provide input to the signal generator, which may be used to trigger and/or modify the dose applied.

Optionally in any of the preceding embodiments the electromagnetic signal comprises symmetrical or asymmetrical pulses having a carrier frequency of about 10 MHz, with a burst duration between about 1 msec and 20 msec (e.g., 10 msec), and a repetition rate between 0.1 and 20 Hz (e.g., 1 Hz). Optionally, in any of the preceding embodiments, the electromagnetic treatment device comprises a set of interchangeable applicators, the set of interchangeable applicators configured to be attachable and removable from the headwear or helmet independent from the circuit control generator.

Optionally, in any of the preceding embodiments, the applicator comprises a flexible printed circuit board.

Other embodiments described provide for devices, systems, and methods for delivering electromagnetic signals and fields to individuals suffering (or at risk from suffering, e.g., following diagnosis) of MS. Such embodiments include a delivery device having an applicator with a plurality or multiple coils capable of delivering an electromagnetic field to a target region. The multi-coil applicator may be made from a metal containing material such as a metal wire. Additionally, the coils of the applicator may be connected to one another by way of a connecting member that is configured to calibrate the frequency of an electromagnetic signal received by the applicator. The connecting member may also connect the multi-coil applicator to a lead or connector that attaches to a power source and/or signal generator.

Some described embodiments provide for an electromagnetic treatment delivery device having a multi-coil applicator configured to apply a therapeutic electromagnetic field to multiple locations on a user's body, wherein the multi-coil applicator comprises a plurality of non-concentric conductive coils. The delivery device may include a control circuit configured to control a generator, wherein the generator is coupled to the multi-coil applicator and configured to provide a pulse-modulated radio frequency signal to the multi-coil applicator to induce the therapeutic electromagnetic field.

Optionally, in any of the preceding embodiments, the electromagnetic treatment delivery device may include a connecting member connecting the plurality of conductive coils to each other and to the generator.

Optionally, in any of the preceding embodiments, the electromagnetic treatment delivery device may include a wearable device (e.g., an article of headwear) configured to be worn by a user, wherein the multi-coil applicator is incorporated into the wearable device.

Optionally, in any of the preceding embodiments, the multi-coil applicator forms a figure eight pattern.

Optionally, in any of the preceding embodiments, the multi-coil applicator comprises pliable and conformable coils having generally circular shapes. Optionally, in any of the preceding embodiments, at least two coils of the multi-coil applicator each have a diameter between about 6 inches to about 8 inches.

Optionally, in any of the preceding embodiments, the multi-coil applicator is configured to generate an electric field on at least two regions of the user's body.

Optionally, in any of the preceding embodiments, the delivery device is incorporated into a bandage.

Optionally, in any of the preceding embodiments, the delivery device includes a sensor configured to monitor a user parameter.

Optionally, in any of the preceding embodiments, the control circuit is configured to control the device to deliver a pre-programmed treatment protocol.

Described herein are also devices, systems and methods for delivering electromagnetic signals and fields configured specifically to accelerate the asymmetrical kinetics of the binding of intracellular ions to their respective intracellular buffers, to enhance the biochemical signaling pathways animals and humans employ in response to the progression of MS.

One variation according to the present invention utilizes repetitive arbitrary non-thermal EMF waveforms configured to maximize the bound concentration of intracellular ions at their associated molecular buffers to enhance the biochemical signaling pathways living systems employ in response to the progression of MS. Non-thermal electromagnetic waveforms are selected first by choosing the ion and the intracellular binding protein, for example $Ca^{2+}$ and CaM, among the many ion-buffer combinations within the living cell, which determines the frequency range within which the signal must have non-thermal frequency components of sufficient, but non-destructive, amplitude to accelerate the kinetics of ion binding. Signals comprise a pulse duration, random signal duration or carrier period which is less than half of the ion bound time to increase the voltage in the target pathway so as to maximally accelerate ion binding to maximally modulate biochemical signaling pathways to enhance specific cellular and tissue responses to nervous system injury from stroke, traumatic brain injury, head injury, cerebral injury, neurological injury, neurodegenerative diseases and cognitive impairment.

In some variations, signals comprise bursts of at least one of sinusoidal, rectangular, chaotic or random EMF wave shapes; have burst duration about 10 msec, with frequency content of about 10 MHz, repeating about 1 Hz. Peak signal amplitude in the ion-buffer binding pathway is less than about 1000 V/m.

Although the methods described herein may operate with signals within the 1 to about a 50 millisecond burst of radio frequency sinusoidal waves in the range of about 1 to about 100 MHz, incorporating radio frequencies in the industrial, scientific and medical (hereinafter known as ISM) band, for example 27.12 MHz, but it may be 6.78 MHz, 13.56 MHz or 40.68 MHz in the short wave frequency band, repeating between about 0.1 and about 100 bursts/sec, such waveforms may not be optimal. As will be discussed in more detail below, PEMF signals having a 10 MHz carrier frequency at about 10 msec burst width (e.g. between about 1 msec and 20 msec) and a rep rate of about 1 Hz (e.g., between about 0.5 and 10 Hz) at very low peak induced magnetic fields (e.g., between about 1 and 200 miliGauss) result in the unexpectedly increase in efficacy by more than 20% compared to PEMF signals outside of these ranged (e.g., using ISM band (such as 27.12 MHz and harmonics) carrier frequencies.

Any of the waveforms described herein can be delivered via inductive coupling with a coil applicator or via capacitive coupling with electrodes in electrochemical contact with the conductive outer surface of the target.

Some embodiments described provide for a waveform configuration that accelerates the kinetics of $Ca^{2+}$ binding to CaM, consisting of about a 1 to about a 10 msec burst of between about 5 MHz to about 50 MHz including frequencies in the ISM band, repeating between about 1 and about 5 bursts/sec and inducing a peak electric field between about 1 and about 100 V/m, then coupling the configured waveform using a generating device such as ultra-lightweight wire or printed circuit coils that are powered by a waveform configuration device such as miniaturized electronic circuitry.

Other embodiments described provide for a waveform configuration that accelerates the kinetics of $Ca^{2+}$ binding to CaM, consisting of about a 1 to about a 10 msec burst of 27.12 MHz radio frequency sinusoidal waves, repeating between about 1 and about 5 bursts/sec and inducing a peak electric field between about 1 and about 100 V/m, then coupling the configured waveform using a generating device such as ultra-lightweight wire, printed circuit coils or conductive garments that are powered by a waveform configuration device such as miniaturized electronic circuitry which is programmed to apply the aforementioned waveform at fixed or variable intervals, for example for 1 minute every 10 minutes, or for 10 minutes every hour, or for any other regimen found to be beneficial for a prescribed treatment. Further embodiments provide for methods and devices for applying electromagnetic waveforms to animals and humans that accelerate the asymmetrical kinetics of the binding of intracellular ions to their associated intracellular buffers, by configuring the waveforms to contain repetitive and/or non-repetitive frequency components of sufficient amplitude to maximize the bound concentration of the intracellular ion to its associated intracellular buffer, thereby to enhance the biochemical signaling pathways living tissue employ in response to the progression of MS.

Additional embodiments provide for methods and devices for applying electromagnetic waveforms to animals and humans which accommodate the asymmetrical kinetics of the binding of $Ca^{2+}$ to CaM by configuring the waveforms to contain repetitive and/or non-repetitive frequency components of sufficient amplitude to accelerate and increase the binding of $Ca^{2+}$ to CaM, thereby enhancing the CaM-dependent nitric oxide (NO)/cyclic guanosine monophosphate (cGMP) signaling pathway.

Further embodiments provide for electromagnetic waveform configurations to contain repetitive and/or non-repetitive frequency components of sufficient amplitude to accelerate and increase the binding of $Ca^{2+}$ to CaM, thereby enhancing the CaM-dependent NO/cGMP signaling pathway to accelerate blood and lymph vessel dilation for delaying the onset and/or severity of MS.

Another aspect of the present invention is to configure electromagnetic waveforms to contain repetitive and/or non-repetitive frequency components of sufficient amplitude to accelerate and increase the binding of $Ca^{2+}$ to CaM, thereby enhancing the CaM-dependent NO/cGMP signaling pathway, or any other signaling pathway, to enhance angiogenesis and microvascularization for delaying the onset and/or severity of MS.

A further aspect of the present invention is to configure electromagnetic waveforms to contain repetitive and/or non-repetitive frequency components of sufficient amplitude to accelerate and increase the binding of $Ca^{2+}$ to CaM, thereby enhancing the CaM-dependent NO/cGMP signaling pathway, or any other signaling pathway, to accelerate deoxyribonucleic acid (hereinafter known as DNA) synthesis by living cells.

Another aspect of the present invention is to configure electromagnetic waveforms to contain repetitive and/or non-repetitive frequency components of sufficient amplitude to accelerate and increase the binding of $Ca^{2+}$ to CaM, thereby enhancing the CaM-dependent NO/cGMP signaling pathway to up- or down-regulate specific genes (messenger ribonucleic acid, mRNA) which control growth factor release, such as basic fibroblast growth factor (bFGF), vascular endothelial growth factor (VGEF), bone morphogenic protein (BMP), or any other growth factor production by living cells.

Another aspect of the present invention is to configure electromagnetic waveforms to contain repetitive and/or non-repetitive frequency components of sufficient amplitude to accelerate and increase the binding of $Ca^{2+}$ to CaM, thereby enhancing the CaM-dependent NO/cGMP signaling pathway to modulate growth factor release, such as basic fibroblast growth factor (bFGF), vascular endothelial growth factor (VGEF), bone morphogenic protein (BMP), or any other growth factor production by living cells.

It is yet another aspect of the present invention to configure electromagnetic waveforms to contain repetitive and/or non-repetitive frequency components of sufficient amplitude to accelerate and increase the binding of $Ca^{2+}$ to CaM, thereby enhancing the CaM-dependent NO/cGMP signaling pathway to up regulate or down regulate specific genes (mRNA) which modulate growth factor and cytokine release, such as basic fibroblast growth factor (bFGF), vascular endothelial growth factor (VGEF), bone morphogenic protein (BMP), IL-1β, or any other growth factor or cytokine production living cells employ in response to the progression of MS.

Another aspect of the present invention is to configure electromagnetic waveforms to contain repetitive and/or non-repetitive frequency components of sufficient amplitude to accelerate and increase the binding of $Ca^{2+}$ to CaM, thereby enhancing the CaM-dependent NO/cGMP signaling pathway, or any other signaling pathway, to modulate cytokine, such as interleukin 1-beta (IL-1β), interleukin-6 (IL-6), or any other cytokine production by living cells, as well as to up regulate or down regulate the associated gene(s) (mRNA).

Another aspect of the present invention is to configure electromagnetic waveforms to contain repetitive and/or non-repetitive frequency components of sufficient amplitude to accelerate and increase the binding of $Ca^{2+}$ to CaM, thereby enhancing the CaM-dependent NO/cGMP signaling pathway, or any other signaling pathway, to modulate cytokine, such as interleukin 1-beta (IL-1β), interleukin-6 (IL-6), or any other cytokine production by living cells in response to MS.

Another aspect of the present invention is to configure electromagnetic waveforms to contain repetitive and/or non-repetitive frequency components of sufficient amplitude to accelerate and increase the binding of $Ca^{2+}$ to CaM, thereby enhancing the CaM-dependent NO/cGMP signaling pathway, or any other signaling pathway, to accelerate or decelerate the production of intra- and extra-cellular proteins by up regulating or down regulating the appropriate gene(s) (mRNA) for tissue repair and maintenance.

It is another aspect of the present invention to configure electromagnetic waveforms to contain repetitive and/or non-repetitive frequency components of sufficient amplitude to accelerate and increase the binding of $Ca^{2+}$ to CaM, thereby enhancing the CaM-dependent NO/cyclic adenosine monophosphate (cAMP) signaling pathway, or any other signaling pathway, to modulate cell and tissue differentiation.

It is yet another aspect of the present invention to configure electromagnetic waveforms to contain repetitive and/or non-repetitive frequency components of sufficient amplitude to accelerate and increase the binding of $Ca^{2+}$ to CaM, thereby enhancing the CaM-dependent NO/cAMP signaling pathway, or any other signaling pathway, to prevent or reverse neurodegeneration and/or to delay the progression and/or reduce the severity of MS.

It is yet another aspect of the present invention to configure electromagnetic waveforms to contain repetitive and/or non-repetitive frequency components of sufficient amplitude to accelerate and increase the binding of $Ca^{2+}$ to CaM, thereby modulating the CaM-dependent NO/cAMP signaling pathway, or any other signaling pathway, to modulate the neurotransmitter releases.

Another aspect of the present invention is to configure electromagnetic waveforms to contain frequency components of sufficient amplitude to accelerate the binding of $Ca^{2+}$ to CaM, thereby enhancing the CaM-dependent NO/cGMP signaling pathway to modulate heat shock protein release from living cells.

Other embodiments provide for methods and devices to improve neuronal survival.

EXAMPLES

Progressive forms of MS, including PPMS and SPMS, are associated with brain atrophy and loss of neurons, axons, and synaptic density, among other pathological features. In contrast to relapsing-remitting (RRMS) disease, many progressive MS cases exhibit less blood brain barrier (BBB) breakdown and greater compartmentalization of inflammation within the central nervous system (CNS), marked by meningeal accumulation of activated T cells, B cells, and macrophages and extensive microgliosis. These inflammatory features are believed to contribute to the cortical grey and white matter pathology that underlies cumulative motor, sensory, and cognitive deficits that are observed in chronic MS progression. Described herein are therapeutic strategies that are anti-inflammatory and neuroprotective, and can effectively be delivered to the CNS are needed. Currently the only approved therapy available for SPMS is mitoxantrone, which can cause a variety of severe adverse reactions and is rarely used. No treatments have shown efficacy in slowing the disability of PPMS. Additionally, development of new drug therapies is hindered by finding agents that can cross the BBB.

In the proposed studies, a PEMF device is used as an innovative non-invasive intervention for PPMS and SPMS. Any of these devices may be used with (e.g., in addition to) or without any drug therapy. Clinical trials have demonstrated that this PEMF therapy is safe and that post-surgical treatment reduced inflammatory cytokine production in wound exudate, and also reduced pain and narcotic use. A pilot study in humans demonstrated that PEMF treatment enhanced cognitive performance during a multitasking exercise. Preclinical work has shown that PEMF treatment reduces the severity of clinical signs in mice with EAE and reduces inflammatory cytokine production in the cerebrospinal fluid after traumatic brain injury. Remarkably, in vitro studies of primary cortical neurons demonstrated that 15 minutes of PEMF treatment reduced hypoxia-induced apoptosis by 50%, suggesting potent neuroprotective effects. Our PEMF device induces a low-amplitude electric field that is significantly below the threshold of neuronal depolarization and has no known adverse effects. Importantly, due to the physics of PEMF (i.e., induction), the electric field delivered to the brain is unimpeded by the skull and/or spine and the BBB, which is a distinct advantage over pharmacologic treatments that may not be able to traverse the BBB. Our preliminary data demonstrate that PEMF therapy has neuroprotective, anti-inflammatory, and pro-cognitive effects that can be delivered to the CNS, that in the context of progressive MS, may strategically (via neuroprotection and suppression of local inflammation and cytotoxicity) hamper the pace of disease progression and facilitate recovery of function. Thus, PEMF treatment has significant potential as a portable, safe, breakthrough therapy for progressive forms of MS.

There are no known PEMF/drug interactions making PEMF an ideal adjunct to any other current and foreseeable treatment regimens. Further, given the lack of immune modulatory drugs for progressive MS, PEMF therapy would offer an inexpensive, safe intervention to slow decline or improve function.

Key preclinical findings have demonstrated that PEMF treatment markedly reduced IL-1p production in the cerebral spinal fluid of rodents with traumatic brain injury, significantly decreased infarct volume after cerebral stroke, and attenuated clinical disease severity in EAE. PEMF treatment also has been shown to substantially increase neuronal survival in primary cortical neurons deprived of oxygen and glucose. The neuroprotective, anti-inflammatory, and pro-cognitive features of PEMF therapy paired with its ability to penetrate the CNS and excellent safety profile make it a promising candidate for progressive MS treatment.

PEMF treatment with cognitive training will likely positively impact cognition, MRI outcomes, disability, mood, and quality of life by promoting neuroprotection and reducing CNS inflammation and cytotoxicity, which, in turn, may slow disease progression and create an opportunity for repair and recovery of function. Preliminary data demonstrate that PEMF therapy has neuroprotective, anti-inflammatory, and pro-cognitive effects that can be delivered to the CNS, which, in the context of progressive MS, may retard disease progression and provide an opportunity for repair and recovery of function.

Two randomized double-blind placebo-controlled post-surgical trials in humans have demonstrated that PEMF treatment was associated with significant reductions in pain, pain medication use, and marked reductions in wound exudate IL-1β, a prototypical inflammatory cytokine in both the periphery and within the CNS. More recent work has been aimed toward determining the utility of PEMF treatment in a variety of models of neurological insults. Rodents treated with PEMF after a closed-head traumatic brain injury exhibited significantly lower levels of IL-1β in the cerebral spinal fluid (CSF), an outcome associated with reduced neuropathology and enhanced recovery of function. Similarly, PEMF-treated rodents with a penetrating TBI had 5-fold less IL-1β in the CSF 18 hours after injury. PEMF treatment has also been shown to reduce infarct size and post-stroke inflammation following distal middle cerebral artery occlusion in mice. PEMF-treated animals exhibited reduced pro-inflammatory and apoptotic cytokine gene expression (IL-1α, TNF, FasL), increased anti-inflammatory and neuroprotective cytokine gene expression (IL-10, IL-11) and, importantly, a significant reduction (−24%) in the volume of the infarct.

PEMF treatment has been shown to be highly neuroprotective in an in vitro neuronal insult model. Primary cortical neurons were subjected to oxygen and glucose deprivation (OGD) for 2 hours and at the onset of OGD were treated with PEMF for 0, 5, 15, 30, or 60. After 2 hours of OGD, cells were re-oxygenated and cultured in standard medium for 24 h and then stained for terminal deoxynucleotidyl transferase (TUNEL), a marker of DNA fragmentation and cell death. 50% fewer dead cells were found in cultures treated with PEMF for 15 minutes or more indicating enhanced survival and neuroprotection of challenged neurons. See, e.g., FIG. 6.

Figures 7A, 7B:
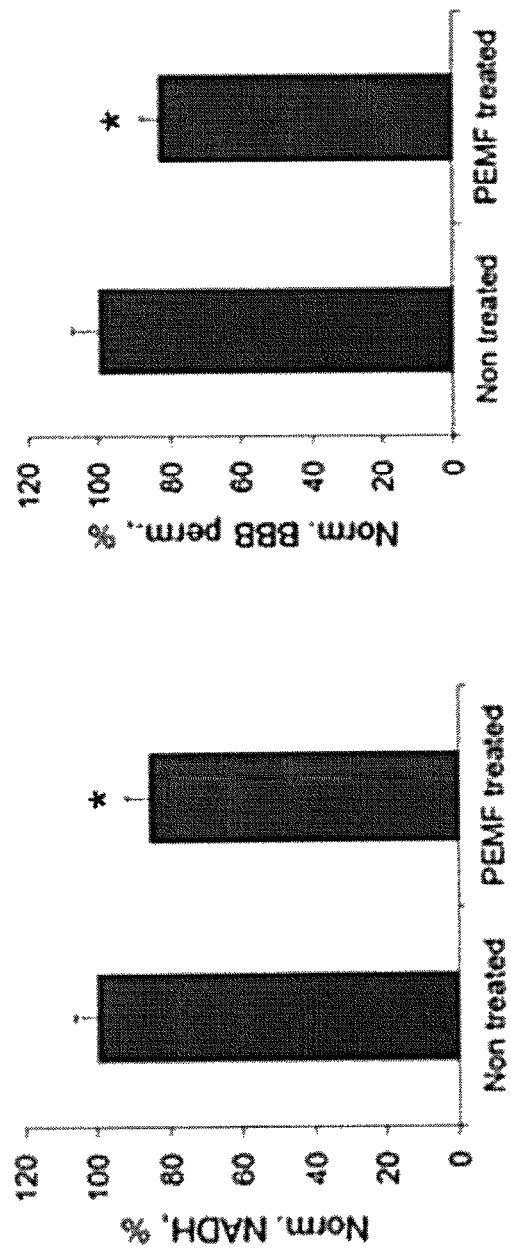
FIG. 7A is a graph illustrating the reduced tissue hypoxia in PEMF treated rats.
FIG. 7B illustrates a reduced leakage of the blood brain barrier (e.g., permeability) following PEMF treatment.

In another model of brain trauma, high intracranial pressure (ICP) was induced in rodents, and 2-photon microscopy was used to determine the effects of PEMF treatment on vascular function. Following induction of high ICP, PEMF treatment was applied for 30 minutes and imaging continued over 4 hours. Normalized to non-treated rats, NADH fluorescence at 4 hours after ICP increase showed reduced tissue hypoxia in PEMF treated rats (FIG. 7A) and reduced leakage of a fluorescent agent from the vasculature into the parenchyma, suggesting less BBB permeability (FIG. 7B).

Figure 3:
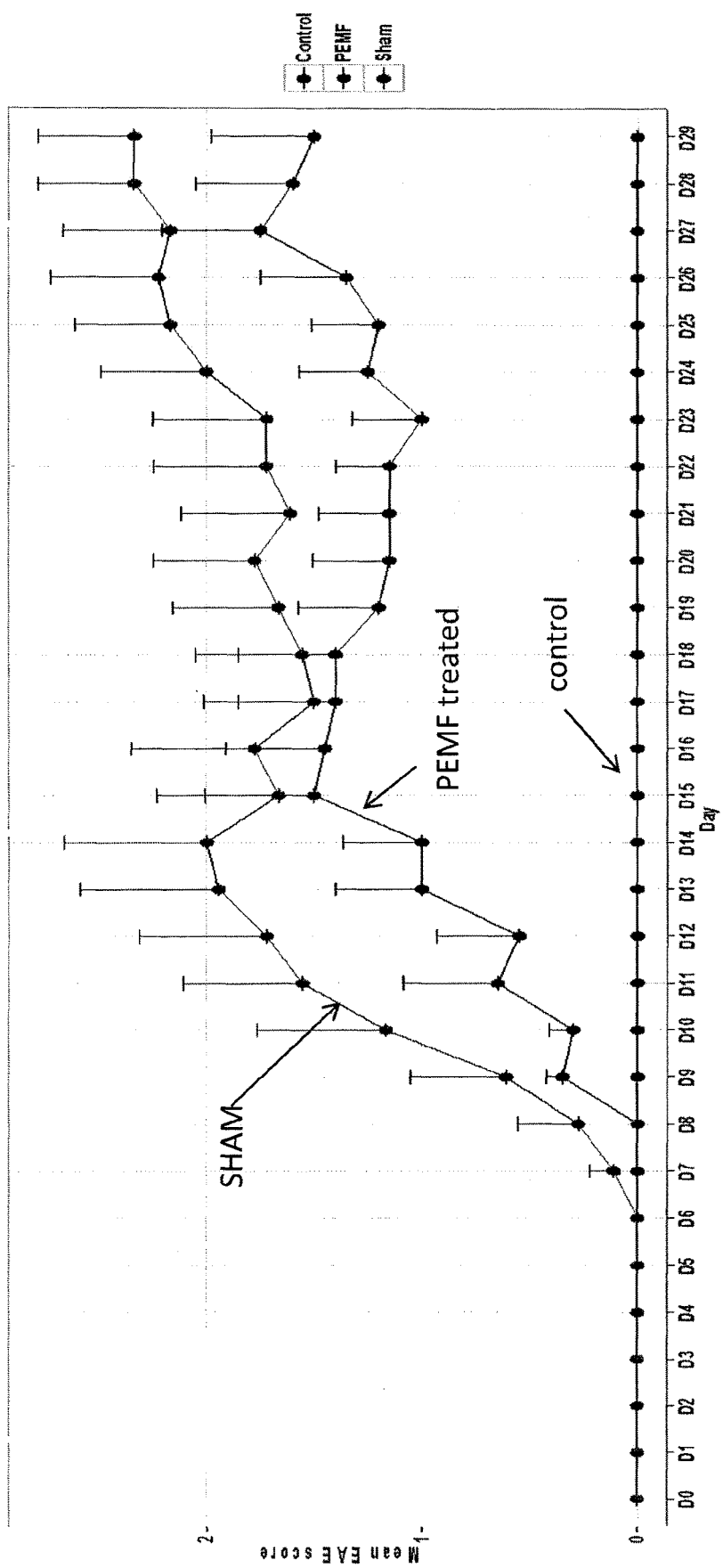
FIG. 3 is a graph showing EAE scores (mean EAE scores) from previous experiments (N=10 per group, less MOG). Note lower overall scores, higher variability, but a similar pattern to FIG. 2.
Figure 5:
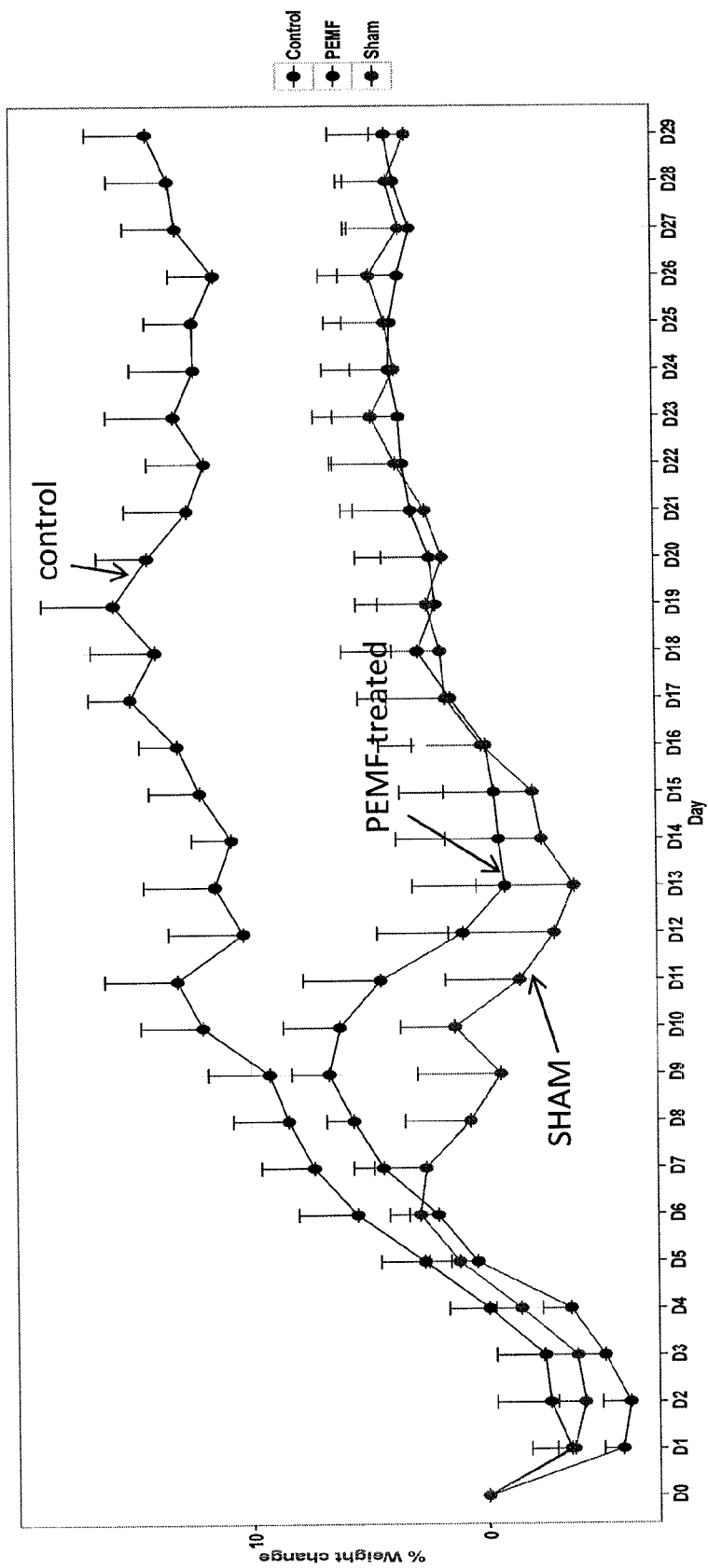
FIG. 5 is a graph showing weight changes from a previous experiment (N=10 per group, less MOG). Note higher variability, but a similar pattern to that shown in FIG. 4.

This data strongly suggests anti-neuroinflammatory and neuroprotective PEMF effects, which is confirmed by studies investigating the utility of PEMF as an intervention for EAE a model of MS. Standard EAE (MOG35-55 in CFA) was induced in female C57B1/6 mice, and body weights and clinical scores (standard 5-pt scale: 0, healthy; 5, moribund/severe paralysis) were recorded daily for 30 days. Starting at the day of disease induction, PEMF or Sham treatment was applied to each cage for 15 minutes twice per day. PEMF treatment delayed the onset of EAE-induced weight loss (FIG. 5) and also delayed the onset of clinical signs and reduced clinical disease severity (FIG. 3). Notably, these clinical trends persisted throughout the 30-day time of observation, suggesting that PEMF treatment could have beneficial effects on long-term MS clinical outcomes.

Pilot studies showed that PEMF treatment during single task and multitask exercises enhanced cognitive performance in healthy human subjects. The participant group that received PEMF treatment during the first half of the experiment showed reduced multitasking cost compared to the other groups that received sham stimulation first. Interestingly, the performance of subjects treated with PEMF in the first half of the experiment was similar to participants in their second trial (after multitask learning had occurred). These results suggest that PEMF treatment did not improve multitasking abilities once the task was learned, rather, PEMF treatment improved the ability of these participants to learn how to multitask faster.

Human studies have illustrated the safety of this PEMF device as a treatment for the head). A human safety trial was recently completed in which PEMF treatment was applied to the heads of 10 healthy young people and no adverse effects related to treatment were observed. A study in 12 healthy volunteers evaluated the effects of PEMF treatment on neuronal recovery, using magneto-encephalography, following physical stimulation. That study showed that PEMF treatment improved neuronal responses and cortical excitability in the treatment condition but not in the sham condition and no adverse effects were reported. An open label study of PEMF treatment in 25 TBI and stroke patients demonstrated that PEMF treatment (15 minutes every 2 hours for 24 hours) is safe for use in this very ill cohort.

Thus, PEMF treatment has been shown to significantly reduce inflammation and pain and enhance cognitive performance in human studies, while preclinical studies have demonstrated that PEMF therapy can markedly attenuate neuroinflammation, reduce post-stroke infarct volume, diminish clinical disease in EAE, support BBB function, and promote survival in challenged neurons. Collectively, these data provide a strong foundation for our rationale that PEMF therapy may be an innovative and safe treatment approach for MS.

In summary, FIGS. 2-5 illustrate example of the use of PEMF to treat MS. For example, in FIGS. 2-5, a mouse model of MS (EAE) was used to assess the effect of twice a day PEMF treatment on MS. In these experiments, 8.5 week old female C57/BL6 mice were treated to induce an MS-like condition and treated with PEMF or sham treated (no PEMF), and compared to control (age/gender matched) mice.

Figure 2:
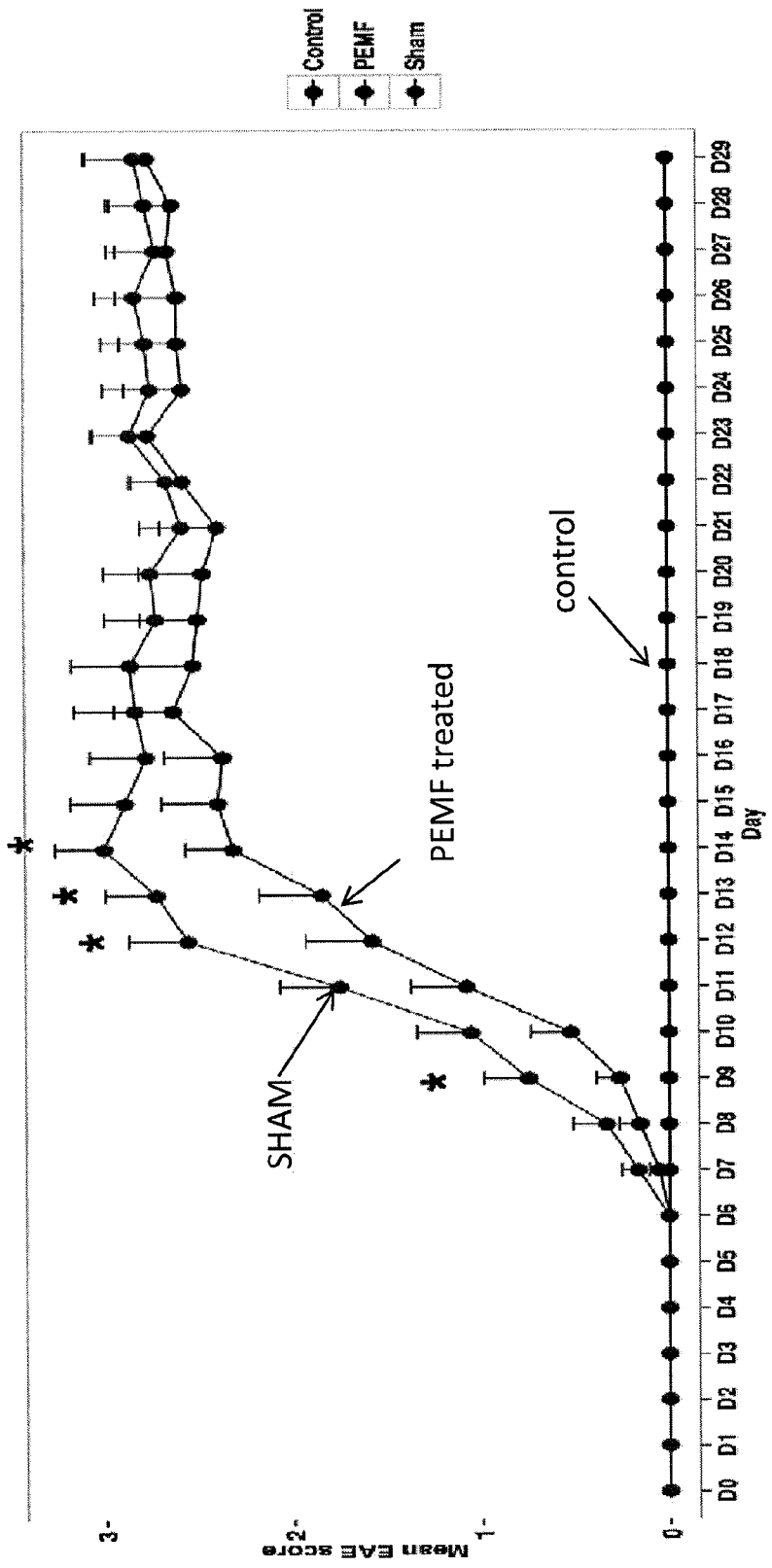
FIG. 2 is a graph showing EAE scores (Experimental Autoimmune Encephalomyelitis scores) in mice including 18 sham (untreated with PEMF), 19 treated (with PEMF) 2× day and control. Note that EAE is a model for the pathogenesis and immune regulation of CD4+ TH1/TH17-mediated tissue damage and is generally considered to be a relevant model for human multiple sclerosis. Between Day 7 and Day 17, the PEM and sham groups were significantly different by 1-way ANOVA.
Figure 4:
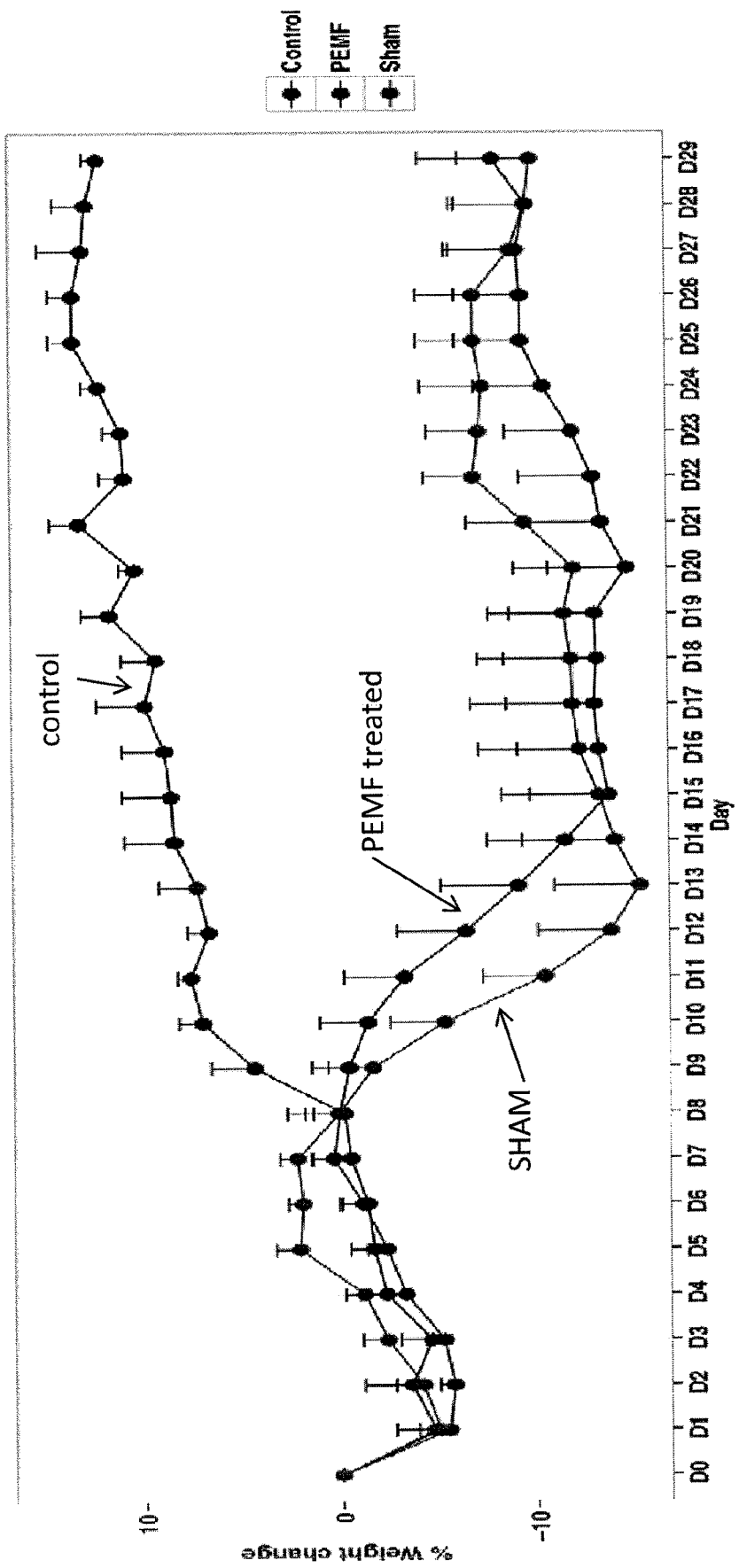
FIG. 4 is a graph showing weight changes (excluding outliner cage with weights that were abnormally low on D0).

For example, in FIGS. 2 and 4, N=19 MOG/CFA+PTX+PEMF, N=19 MOG/CFA+PTX+Sham, and N=4 PBS/CFA+PTX mice were followed for 30 days. 150 ug MOG/mouse in 2×50 ul injections; subcutaneous (combined with CFA), 200 ug CFA/mouse, in 2×50 ul injections; subcutaneous (combined with MOG), and 0.2 ug PTX/mouse, in 1×100 ul injection; IP; repeated on D2. MOG/CFA or PBS/CFA was injected on D0 between 3 pm-5:30 pm, and PTX was injected on D0 between 3 pm-5:30 pm and repeated on D2 between 9 am-10 am.

PEMF stimulation started on D1 (7:30 am) and was repeated every day until D29 twice a day, morning (7:30-10 am) and evening (4-6 pm), 30 min each time. Sham stimulation was the same as PEMF except the units were turned off. PEMF cages (B (5), D (5), F (5), H (4)) and Sham cages (C (5), E (5), G (5), I (4)) were compared to a similarly housed control (PBS) cage (A (4)). On even number days, PEMF stimulation came before sham and on odd number days, sham before PEMF (counting 0 as even number). Mice were weighed and scored during morning stimulation every day. Mouse cecal samples were collected during evening stimulation, 3 times during the study (D4-D6, D14-D16, D24-D26). The stimulator was tested at least every week (D-2, D5, D10, D17, D25). Mice were sacrificed and samples collected: spleen, brain, spinal cord, lymph nodes. On D30 (A1-A3, B1, B2, C2, D1, D3, E1-E3).

As shown in FIG. 3, the mean EAE score with and without PEMF was significantly different between sham and PEMF-treated mice, particularly over D7 to D14. During this time, there was a marked decrease in the severity of the MS and/or a delay in the onset based on EAE score. A similar effect is seen in other data, as shown in FIG. 3. In FIG. 3, the dosing of the EAE effect was lower than in the data shown in FIG. 2. Similarly, in FIGS. 4 and 5, the effect of mouse weight in treated vs. untreated mice is shown.

Figure 6:
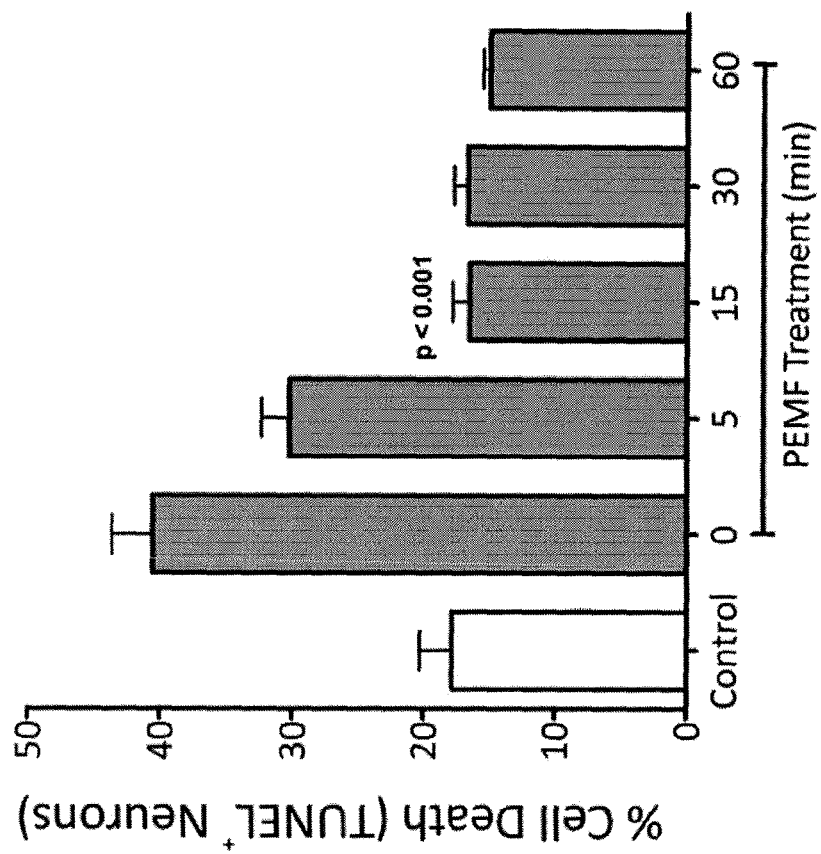
FIG. 6 is a graph illustrating a time course for the neuroprotective effect of PEMF on neurons in cell culture.

This evidence of anti-inflammatory effects of the PEMF devices described herein has been further confirmed by EAE experiments demonstrating a reduction in EAE severity of clinical signs and a delay in onset of disease. Though this is consistent with anti-neuroinflammatory effects seen in previous data, EAE/MS are autoimmune diseases that differ from TBI or stroke and involve unique processes of inflammation, blood brain barrier permeability, and neurodegeneration. As shown in FIG. 6, challenged neurons are markedly protected from apoptosis by a single 15-minute (or longer) exposure to PEMF. Additionally, activated microglial inflammation (an important driver of CNS inflammation) is markedly reduced after 1 15-minute PEMF exposure (similar data in astrocytes, to a lesser magnitude). This neuroprotection data were a significant surprise, as there was little expectation of a pro-survival effect, particularly to the extent it was observed. PEMF may therefore provide substantial anti-neuroinflammatory and neuroprotective effects.

For example, RRMS patients (~85% of the MS population) currently have a variety of treatment options available that can minimize relapse frequency and severity. However, the treatments do not stop disease progression nor address all consequences of the disease. Patients often have problems with fatigue, mood, cognition, and reduced quality of life. Most RRMS patients will transition to secondary progressive SPMS after a period of time, a phase in which there is steady worsening of disease. Progressive MS patients (including primary progressive and secondary progressive), have few to no treatment options. RRMS therapies are not effective for progressive MS patients and this is believed to be, in part, because there is less peripheral immunity-driven disease progression, rather a neurodegenerative and neuroinflammatory process that is compartmentalized in the CNS, leaving drug-therapies without effect because of an intact blood brain barrier. As such, treatments that are capable of reaching the CNS (i.e., PEMF) may be particularly important for the future of progressive MS therapeutics.

Figure 8:
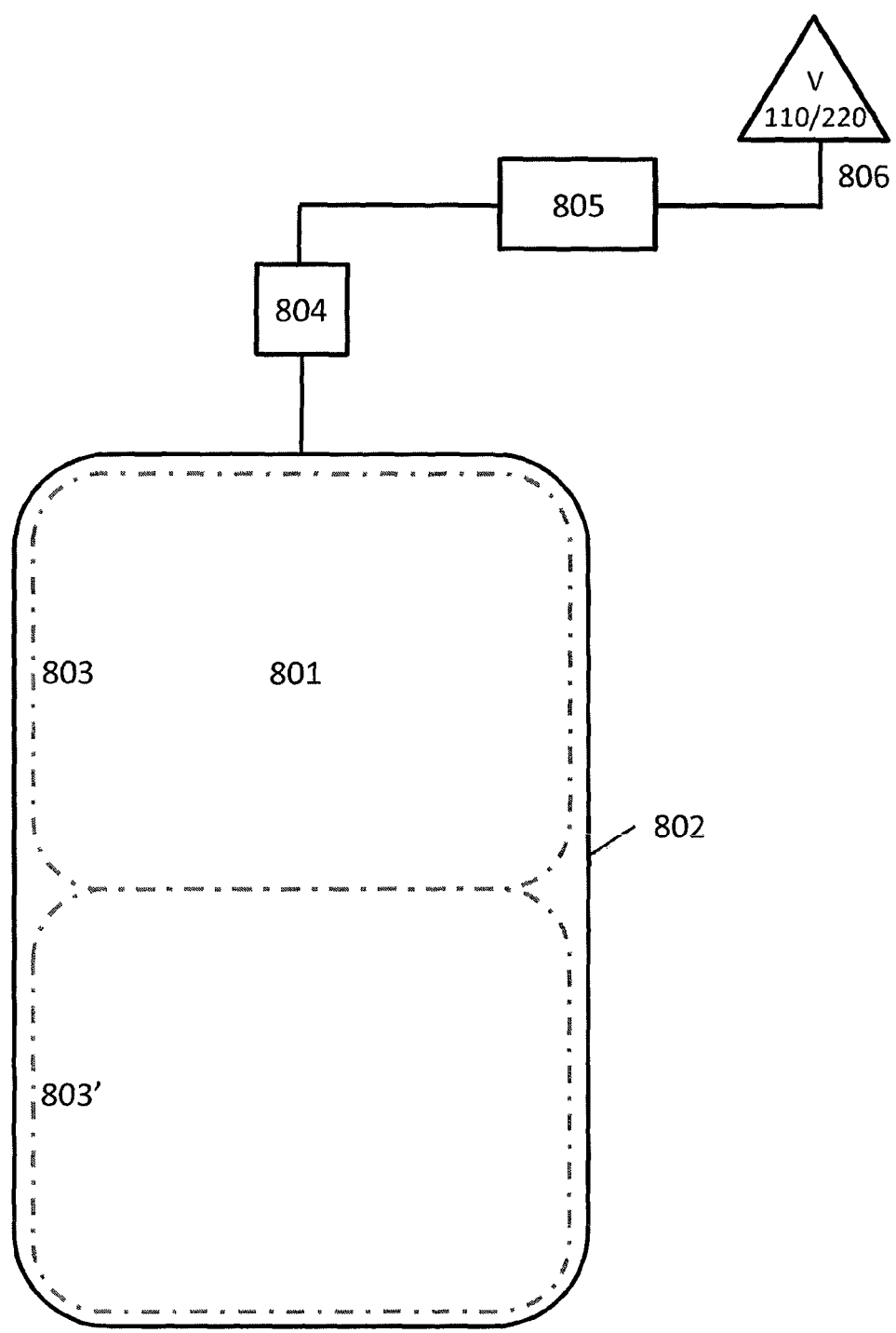
FIG. 8 illustrates one example of an apparatus, configured as a mat, for treating a patient with MS as described herein.

FIGS. 8 and 9 illustrate examples of apparatuses that may be used to deliver the therapies described herein. For example, FIG. 8 is a schematic of a mat that may be used to deliver PEMF as described. In FIG. 8, the foam mat 802 includes two (though one or more than 2 may be incorporated) embedded PEMF applicator coils 803, 803'. Within the coil region is a therapeutic space 801 onto which the patient's head and/or neck and/or spine may be placed. A user control module 804 may connect to a power supply 806 (e.g., 110/120 wall plug, battery, etc.) and signal generator 805. Any of these apparatuses may also include a sensor (not shown) such as a pressure sensor and/or motion sensor (e.g., to determine sleep state based on body movements), or the like.

While the benefit of PEMF may be solely be related to CNS tissue exposure, it is also possible that treating non-CNS tissue in the context of MS would be valuable. For example, secondary lymphoid organs like spleen and lymph nodes may be important activity sites for the pathogenesis of the autoimmune cascade before and during the infiltration/damage of the brain and spinal cord. Thus a patient laying from head to bottom of torso on the mat shown in FIG. 8 may effectively treat the brain and spinal cord as well as peripheral blood and secondary lymphoid organs with the therapeutic PEMF field. The added benefit of the mat may be that the head and spinal cord can be treated simultaneously. The mat could also be integrated into a bed for optimal timing of treatments at night and/or while sleeping.

FIG. 9 illustrates another example of an apparatus as described herein, configured as a wearable garment to be worn over the patient's torso for treating a neurological disorder (such as MS) which may affect the spinal column and brain stem. In this example, the apparatus can be used on its own or in addition to one or more additional applicators (e.g., head-wearable applicators, etc.), particularly for patients who have evidence or suspicion of brainstem or spinal cord lesions. This wearable apparatus could be used to minimize or prevent future brain stem or spinal cord damage.

In FIGS. 9A and 9B, the device 901 is a torso-wearable garment that includes an integrated power supply, signal generator and control (e.g., power supply) 902 positioned on the garment so that it can be controlled/contacted by the user. FIG. 9A shows a front view and FIG. 9B a back view. The garment may also include a connection (e.g., wiring) from the signal generator to the PEMF applicators (e.g., coils 906, 907, shown here as ensheathed within vest fabric). The garment in this example also includes a reinforced high collar 904 into which one of the applicators have been integrated. Wiring 905 connects each of the coils 906, 907, including the brain stem and cervical spinal cord treating coil 906 and the plurality of spinal cord treating coils 907. The reinforced high collar may ensure that the entire spinal cord and brainstem are treated.

Any of the devices described herein may be used to deliver PEMF treatment to a patient in need of the neuroprotective effects described above. For example, returning to FIG. 6, primary neurons were exposed to $2h$ of oxygen and glucose deprivation (OGD), then reoxygenated for 24 h and stained for TUNEL (death). Some cultures were treated with PEMF (5, 15, 30, 60 m) at the onset of OGD. Unchallenged cultures had 20% cell death, OGD with no PEMF had 40% cell death, and OGD with PEMF≥15 mins had 20% cell death or complete protection from the insult. Notably, 15, 30, and 60 minutes were not differentiable in terms of protection.

FIGS. 10A-10H and 11A-11D illustrate the effects of PEMF on microglia and astrocytes, respectively. Primary microglia and astrocytes were cultured separately and exposed to LPS (a commonly used activation reagent) and exposed to PEMF or sham for 15 minutes at the onset of LPS stimulation. Cytokines were later collected for multiplex analysis at 24 h. Microglia (and to a lesser extent astrocytes) demonstrated marked reductions in pro-inflammatory cytokines and chemokines after one 15 minute PEMF treatment.

Figure 10A:
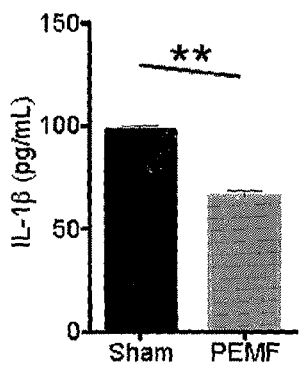
FIGS. 10A-10H illustrate the effect of PEMF treatment on various cytokines in microglia, generally illustrating a reduction in inflammatory cytokines following PEMF treatment as described herein.
Figure 10B:
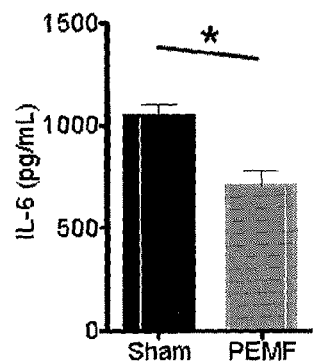
Figure 10C:
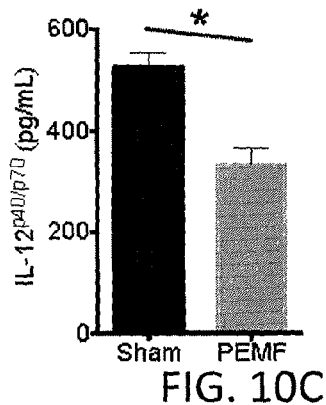
Figure 10D:
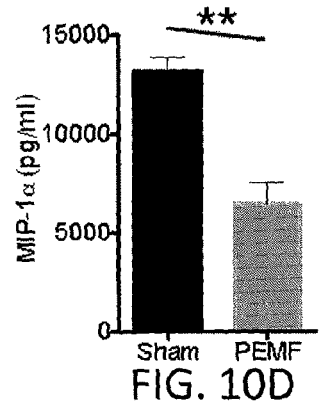
Figure 10E:
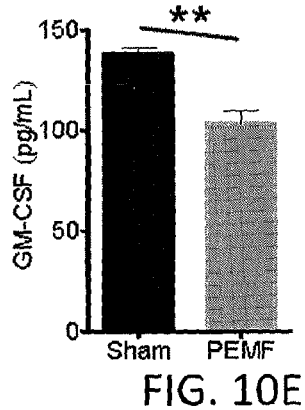
Figure 10F:
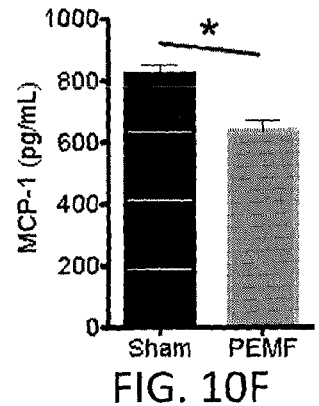
Figure 10G:
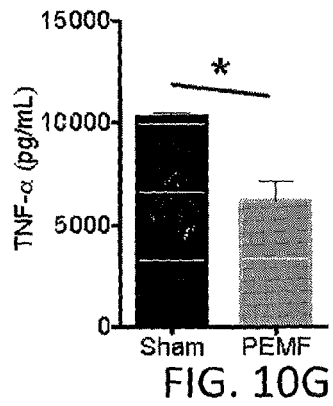
Figure 10H:
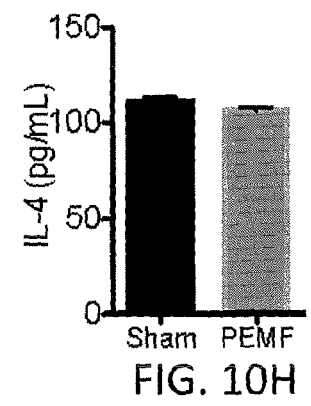
Figure 11A:
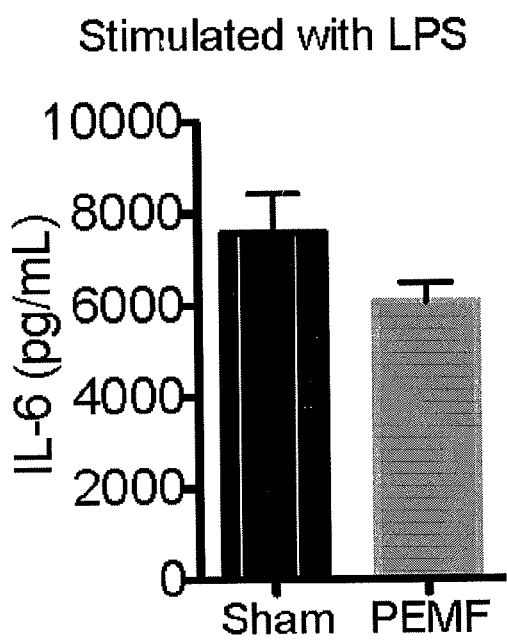
FIGS. 11A-11D illustrate the effect of PEMF treatment on various cytokines in astrocytes, illustrating a reduction in inflammatory cytokines following PEMF treatment as described herein.
Figure 11B:
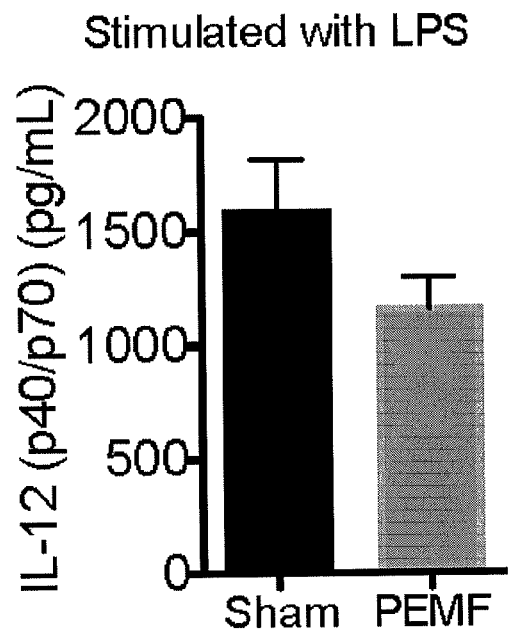
Figure 11C:
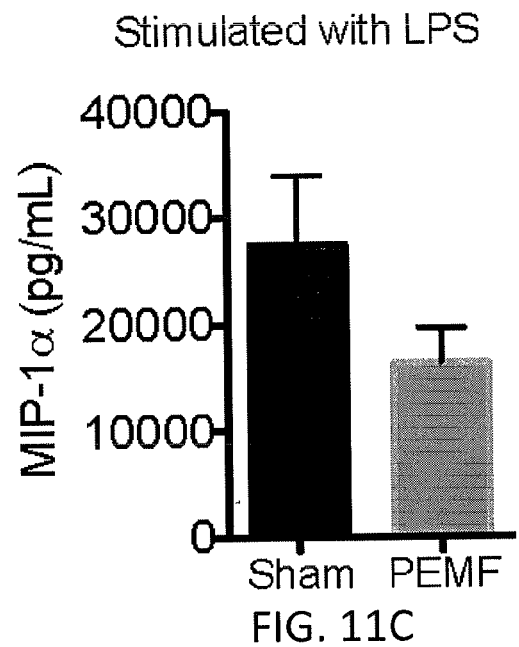
Figure 11D:
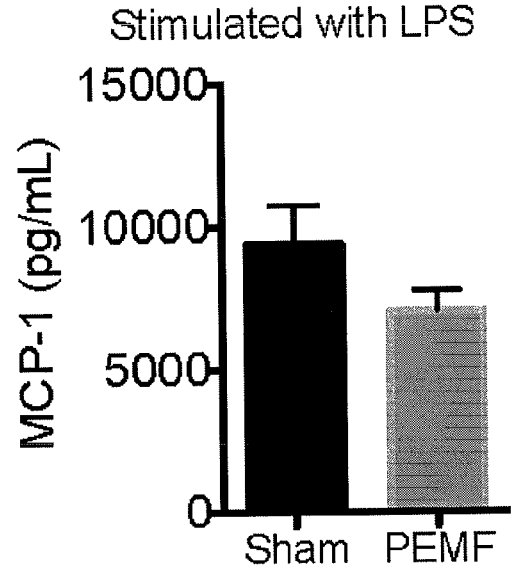

For example, FIGS. 10A-10H show a reduction in IL-1β (FIG. 10A), IL-6 (FIG. 10B), IL-12 (FIG. 10C), MIP-1α (FIG. 10D), GM-CSF (FIG. 10E), MCP-1 (FIG. 10F), and TNFα (FIG. 10G). No significant effect was seen on IL-4 (FIG. 10H). FIGS. 11A-11D show that, following PEMF treatment as described herein, a reduction in IL-6 (FIG. 11A), IL-12 (FIG. 11B), MIP-1α (FIG. 11C) and MCP-1 (FIG. 11D).

Such data indicates that even a single 15-minute exposure may reduce neuronal apoptosis and microglial inflammation, and therefore clinical effects may occur after as little as a handful treatments. For example, between 2-12 fifteen minute treatments per day for greater than one week, two weeks, 3 weeks, 4 weeks, 2 months, 3 months, 4 months, 5 months, 6 months, 1 year, 2 years, 3 years, 4 years, 5 years, 6 years, etc. may be used. When applying for greater than a few months, the signal may be modulated as described herein to prevent desensitization.

Figure 12:
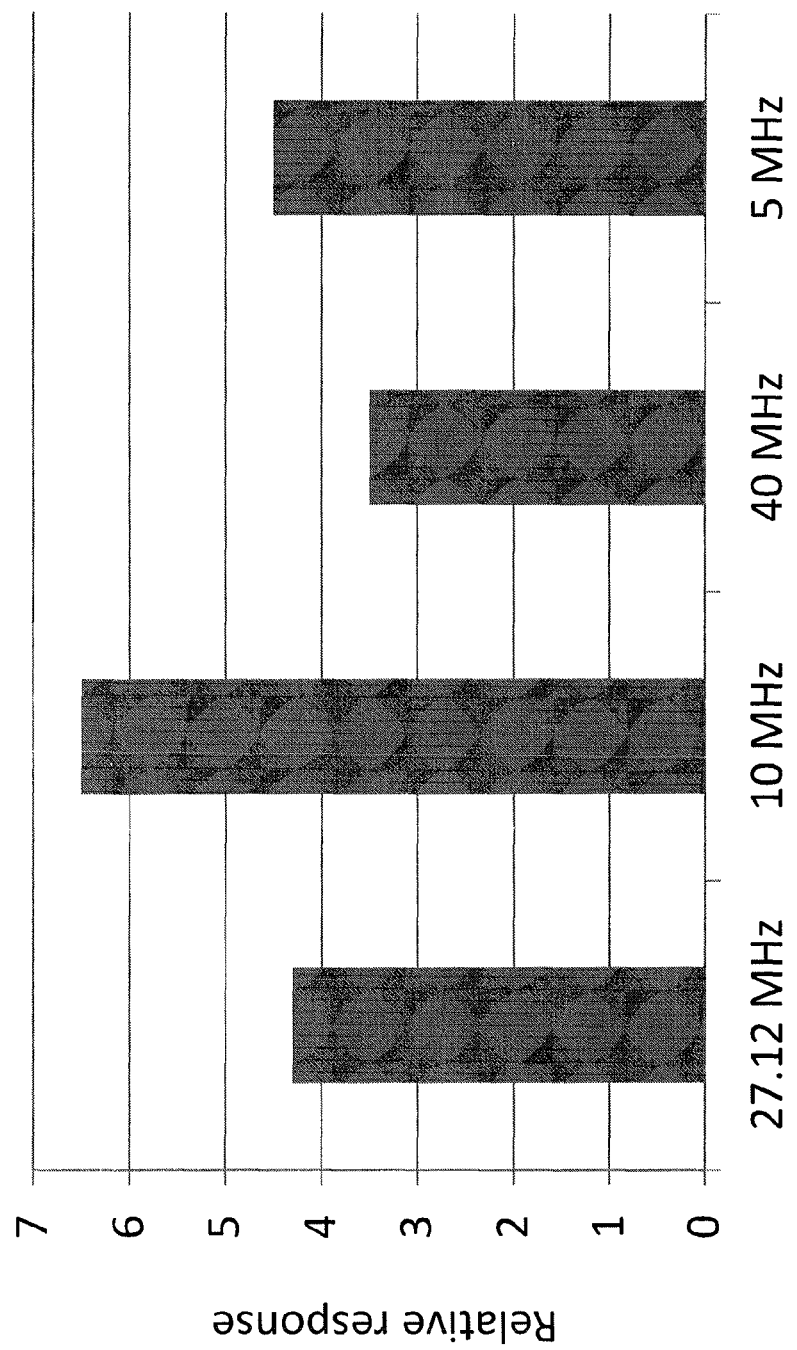
FIG. 12 is a graph describing the relative neuroprotective effects of PEMF signal parameters (in this example, highlighting the carrier frequency).

In general, the methods and apparatuses described herein may include a signal that is adapted to treat a neurological disorder. For example, a PEMF signal having parameters centered around a carrier frequency of 10 MHz, with burst duration of about 10 msec, and a burse frequency of about 1 Hz rep rate (thus a longer burst width than previously applied) may have substantially and surprisingly increased efficacy. This has been seen in a cell culture, showing an increase in outcome by about 20% compared to values outside of this range (see, e.g., FIG. 12).

As mentioned above, the signal generator (pulse generators) described herein may also be adapted to prevent or limit desensitization (e.g., habituation, accommodation, etc.) of the patient to the applied PEMF signals. Preliminary data has suggested that desensitization may be particularly problematic when treating neurodegenerative disorders such as MS using the apparatuses described herein. For example, although PEMF works well acutely (e.g., delivering a dose of 15 min every 2 h for 72 h), chronic administration of PEMF, as might be necessary in the context of neurodegenerative diseases or MS, may elicit waning responses to the treatment over time as the body adapts to the stimulus and/or downstream signaling pathways are dampened by repeated activation.

Described herein are dose regimes in which subsequent doses vary one or more parameters (e.g., burst duration, burst frequency, amplitude/field strength, etc.) between individual doses. Parameters may be varied within a dose and/or between doses. For example, doses may be varied by varying parameters of the waveform and dosing regimen (within fixed boundaries) either randomly, or with a preset pattern, or some combination thereof. Varying the signals in this manner may minimize attenuation of therapeutic response over time in patients that require chronic treatment (MS or otherwise). For example, parameters that may be varied may include the number of treatments per 24 h (e.g., between 1-12), the duration of treatment (e.g., between 0.2-30 min), the burst width (e.g., between 2 msec-20 msec), the repetition rate (e.g., between 0.5 Hz-5 Hz), and the amplitude (e.g., between 0.001 miliGauss to 200 miliGauss).

In general, any of the methods an apparatuses described herein may also or alternatively apply PEMF based on either the time of day and/or the patient's sleep state (e.g., awake, asleep, asleep in REM, etc.). The circadian cycle in humans controls a number of biological processes. In particular, cortisol (the brake of the immune system) is lowest at night during sleep and this is likely a factor in increased inflammatory tone of the immune system at night. To maximize the anti-inflammatory effect of PEMF in the periphery and CNS, it may be beneficial to treat automatically on a cycle at night or at least once before bed and/or when the patient is asleep or has been asleep for a predetermined length of time. For example, the interstitial space in the brain becomes greater, allowing for flow of cerebrospinal fluid during sleep, which would optimize the delivery of electric field to the tissue.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A therapeutic garment device for treating a neurological condition by pulsed electromagnetic field (PEMF) stimulation, the device comprising:

a torso garment configured to be worn on a subject's torso, the torso garment having a back and a neck portion, the back including a middle region:

a plurality of wire coil PEMF applicators extending down the middle region of the back to treat the subject's spine, wherein the plurality of wire coil PEMF applicators comprises a plurality of substantially coplanar loops arranged adjacent to each other in a line down the back:

a neck wire coil PEMF applicator on the neck portion to treat the patient's brain stem and cervical spine; and a PEMF signal generator integrated into the torso garment, wherein the PEMF signal generator is configured to deliver a treatment dose comprising a PEMF signal, wherein the PEMG signal generator is connected to the plurality of wire coil PEMF applicators and the neck wire coil PEMF applicator.

2. The device of claim 1, wherein the PEMF signal generator is configured to generate the PEMF signal comprising bursts of 10 MHz carrier waves, wherein the bursts repeat at between 0.01 and 10 Hz have a field strength of between 1 and 200 miliGauss.

3. The device of claim 1, wherein the PEMF signal generator is configured to generate the PEMF signal comprising bursts of 10 MHz sinusoidal carrier waves, wherein the bursts repeat at between 0.1 and 5 Hz have a field strength of between 1 and 200 miliGauss.

4. The device of claim 1, wherein the PEMF signal generator is configured to generate the PEMF signal comprising bursts of 10 MHz sinusoidal carrier waves having a burst width of between 5 and 20 msec, wherein the bursts repeat at 1 Hz and have a field strength of between 1 and 200 miliGauss.

5. The device of claim 1, wherein the torso garment is configured as a vest.

6. The device of claim 1, further comprising a power supply integrated into the torso garment.

7. The device of claim 1, wherein the neck portion comprises a reinforced high collar.

8. The device of claim 1, further comprising wiring within a fabric of the torso garment connecting the PEMF signal generator to the plurality of wire coil PEMF applicators and the neck wire coil PEMF applicator.

9. The device of claim 1, wherein the signal generator is configured to limit the number of doses deliverable within a 24 hour period to 12 or less.

10. The device of claim 1, wherein the signal generator comprises a clock and further wherein the signal generator is configured to deliver treatment doses at night.

11. The therapeutic garment device of claim 1, wherein the loops are single-turn loops.

12. A therapeutic garment device for treating multiple sclerosis by pulsed electromagnetic field (PEMF) stimulation, the device comprising:

a torso garment configured to be worn on a subject's torso, the torso garment having a back and a neck portion, the back including a middle region;

a plurality of wire coil PEMF applicators extending down the middle region of the back to treat the subject's spine, wherein the plurality of wire coil PEMF applicators comprises a plurality of substantially coplanar loops arranged adjacent to each other in a line down the back;

a neck wire coil PEMF applicator on the neck portion to treat the patient's brain stem and cervical spine; and a PEMF signal generator integrated into the torso garment, wherein the PEMF signal generator is programmed to deliver a treatment dose comprising a PEMF signal comprising bursts of a 10 MHz carrier wave, wherein the bursts repeat at between 0.01 and 10 Hz, and wherein the PEMF signal generator is connected to the plurality of wire coils applicators and the neck wire coil PEMF applicator.

13. The therapeutic garment device of claim 12, wherein the loops are single-turn loops.

14. A method of treating multiple sclerosis in a patient, the method comprising delivering a dose of pulsed electromagnetic field (PEMF) stimulation having a field strength of between 1 and 200 milliGauss, wherein the PEMF stimulation comprises bursts of a 10 MHz carrier wave, wherein the bursts repeat at between 0.01 and 10 Hz, from one or more PEMF coils positioned against one or more of the patient's head, neck, and spine, wherein the bursts have a field strength of between 1 and 200 milliGauss.

15. The method of claim 14, wherein delivering the PEMF stimulation comprises delivering the PEMF stimulation comprising bursts repeating at 1 Hz.

16. The method of claim 14, wherein delivering the PEMF stimulation comprises delivering the PEMF stimulation comprising bursts having a 10 msec burst width.

17. The method of claim 14, wherein delivering the PEMF stimulation comprises delivering the dose for 15 minutes or less.

18. The method of claim 14, wherein delivering the PEMF stimulation comprises delivering the dose for 15 minutes or less for between one and 12 times a day.

19. The method of claim 14, wherein delivering the PEMF stimulation comprises automatically delivering the dose while the patient is sleeping.

20. The method of claim 14, further comprising determining a patient's sleep state and delivering the PEMF stimulation while the patient is sleeping.

21. The method of claim 14, further comprising applying a plurality of additional doses without desensitizing the patient, wherein the additional doses each have different parameters for one or more of: burst repetition rate, burst widths, and field strength.

22. The method of claim 14, further comprising applying a plurality of additional doses without desensitizing the patient, wherein the additional doses each have different parameters for one or more of: burst repetition rate between 0.01 and 10 Hz, burst widths between 1 msec and 100 msec, and field strength between 1 and 200 miliGauss.

23. The method of claim 14, wherein said stimulation comprises delivering the dose of PEMF stimulation from a plurality of substantially coplanar loops of PEMF coils that are arranged adjacent to each other in a line down the patient's back.

24. The method of claim 23, wherein the loops are coplanar.

25. The method of claim 24, wherein the loops are single-turn loops.

26. A method of treating multiple sclerosis in a patient, the method comprising automatically delivering a dose of pulsed electromagnetic field (PEMF) stimulation having a field strength of between 1 and 200 milliGauss while the patient is sleeping, wherein the PEMF stimulation comprises bursts of a 10 MHz carrier wave repeated at between 0.01 and 10 Hz, further wherein the PEMF stimulation is delivered from a plurality of PEMF coils positioned against one or more of the patient's head, neck, or spine.

27. The method of claim 26, wherein delivering the PEMF stimulation comprises delivering the PEMF stimulation comprising bursts repeating at 1 Hz.

28. The method of claim 26, wherein delivering the PEMF stimulation comprises delivering the PEMF stimulation comprising bursts having a 10 msec burst width.

29. The method of claim 26, wherein delivering the PEMF stimulation comprises delivering the dose for 15 minutes or less.

30. The method of claim 26, further comprising determining a patient's sleep state.

31. The method of claim 26, further comprising applying a plurality of additional doses without desensitizing the patient, wherein the additional doses each have different parameters for one or more of: burst repetition rate, burst widths, and field strength.

32. The method of claim 26, further comprising applying a plurality of additional doses without desensitizing the patient, wherein the additional doses each have different parameters for one or more of: burst repetition rate between 0.01 and 10 Hz, burst widths between 1 msec and 100 msec, and field strength between 1 and 200 miliGauss.

33. The method of claim 26, wherein the PEMF coils comprise a plurality of coplanar loops.

34. The method of claim 33, wherein the loops are single-turn loops.

* * * * *